US009617516B2

(12) United States Patent
Chancellor et al.

(10) Patent No.: US 9,617,516 B2
(45) Date of Patent: Apr. 11, 2017

(54) MUSCLE-DERIVED CELLS (MDCS) FOR PROMOTING AND ENHANCING NERVE REPAIR AND REGENERATION

(75) Inventors: Michael B. Chancellor, Pittsburgh, PA (US); Johnny Huard, Waxford, PA (US); Brandon Minnery, Silver Spring, MD (US); Chistopher C. Capelli, Kenosha, WI (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 661 days.

(21) Appl. No.: 10/832,542

(22) Filed: Apr. 26, 2004

(65) Prior Publication Data

US 2005/0238625 A1  Oct. 27, 2005

Related U.S. Application Data

(60) Provisional application No. 60/465,846, filed on Apr. 25, 2003.

(51) Int. Cl.
*C12N 5/07* (2010.01)
*C12N 5/071* (2010.01)
*C12N 5/16* (2006.01)
*C12N 5/0789* (2010.01)
*C12N 5/077* (2010.01)
*A61K 35/34* (2015.01)
*A61K 35/12* (2015.01)

(52) U.S. Cl.
CPC ............ *C12N 5/0658* (2013.01); *A61K 35/34* (2013.01); *A61K 35/12* (2013.01)

(58) Field of Classification Search
CPC ...... A61K 35/34; A61K 48/00; C12N 5/0658; C12N 2500/84; C12N 2510/00
See application file for complete search history.

(56) References Cited

U.S. PATENT DOCUMENTS

| 4,424,208 A | 1/1984 | Wallace et al. |
| 4,965,353 A | 10/1990 | della Valle et al. |
| 5,026,365 A | 6/1991 | Rossini et al. |
| 5,045,601 A | 9/1991 | Capelli et al. |
| 5,053,050 A | 10/1991 | Itay |
| 5,082,670 A | 1/1992 | Gage et al. |
| 5,130,141 A | 7/1992 | Law et al. |
| 5,206,028 A | 4/1993 | Li |
| 5,336,263 A | 8/1994 | Ersek et al. |
| 5,443,950 A | 8/1995 | Naughton et al. |
| 5,510,254 A | 4/1996 | Naughton et al. |
| 5,516,532 A | 5/1996 | Atala et al. |
| 5,538,722 A | 7/1996 | Blau et al. ............... 424/93.21 |
| 5,541,107 A | 7/1996 | Naughton et al. |
| 5,594,032 A | 1/1997 | Gonzalez-Cadavid et al. |
| 5,656,478 A | 8/1997 | Tanagho et al. |
| 5,667,778 A | 9/1997 | Atala |
| 5,733,337 A | 3/1998 | Carr, Jr. et al. |
| 5,785,964 A | 7/1998 | Naughton et al. |
| 5,833,978 A | 11/1998 | Tremblay |
| 5,842,477 A | 12/1998 | Naughton et al. |
| 5,858,351 A | 1/1999 | Podsakoff et al. |
| 5,858,390 A | 1/1999 | Boss, Jr. |
| 5,858,721 A | 1/1999 | Naughton et al. |
| 5,863,531 A | 1/1999 | Naughton et al. |
| 5,869,041 A | 2/1999 | Vandenburgh |
| 5,876,447 A | 3/1999 | Arnett |
| 5,895,745 A | 4/1999 | Chandler et al. |
| 5,902,741 A | 5/1999 | Purchio et al. |
| 5,962,325 A | 10/1999 | Naughton et al. |
| 6,001,654 A | 12/1999 | Anderson et al. |
| 6,099,832 A | 8/2000 | Mickle et al. |
| 6,121,042 A | 9/2000 | Peterson et al. |
| 6,171,340 B1 | 1/2001 | McDowell |

(Continued)

FOREIGN PATENT DOCUMENTS

| AU | 2006202380 A1 | 6/2007 |
| CA | 2438904 A1 | 9/2002 |
| CN | 1812800 A | 4/2004 |
| EP | 1617852 A2 | 11/2004 |
| JP | 2000287683 A | 10/2000 |
| JP | 2007275613 A | 10/2007 |
| WO | WO-9107992 A1 | 6/1991 |
| WO | WO-9407999 A1 | 4/1994 |
| WO | WO-9421299 A1 | 9/1994 |
| WO | WO 94/25080 | 11/1994 |

(Continued)

OTHER PUBLICATIONS

Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
't Hart et al. Curr. Opin. Neurol. 2003. 16: 375-383.*
Battiston et al. Microsurgery 2000. 20: 32-36.*

(Continued)

*Primary Examiner* — Chang-Yu Wang
(74) *Attorney, Agent, or Firm* — Goodwin Procter LLP; Shovon Ashraf

(57) ABSTRACT

The present invention describes methods involving the use of muscle derived cells (MDCs), preferably obtained from skeletal muscle, to support the innervation and repair of damaged tissues and organs, particularly associated with nerve damage or neuropathy. The invention relates to MDCs for use in methods for promoting or enhancing innervation of nerve cells, particularly in the peripheral nervous system, and their ability to contribute to the development of neuronal tissue when MDCs are introduced at or near a tissue or organ site in need of repair due to injury, damage, disease, or dysfunction. Such methods are useful for the treatment of central and peripheral nervous system disorders and to alleviate, abate, or eliminate the symptoms of neurologic or neurodegenerative diseases in animals, particularly mammals, including humans. The methods are also useful for treating both nerve and muscle tissue following injury, damage, or dysfunction to these tissue types.

3 Claims, No Drawings

(56) References Cited

U.S. PATENT DOCUMENTS

| | | | |
|---|---|---|---|
| 6,174,333 B1 | 1/2001 | Kadiyala et al. | |
| 6,200,606 B1 | 3/2001 | Peterson et al. | |
| 6,261,832 B1 | 7/2001 | Law | |
| 6,299,905 B1 | 10/2001 | Peterson et al. | |
| 6,306,424 B1 | 10/2001 | Vyakarnam et al. | |
| 6,335,028 B1 | 1/2002 | Vogel et al. | |
| 6,337,184 B1 | 1/2002 | Miller | |
| 6,348,069 B1 | 2/2002 | Vacanti et al. | |
| 6,482,645 B2 | 11/2002 | Atala | |
| 6,497,872 B1 | 12/2002 | Weiss et al. | |
| 6,503,504 B1 | 1/2003 | Vandenburgh | |
| 6,682,761 B2 | 1/2004 | Pace et al. | |
| 6,986,735 B2 | 1/2006 | Abraham et al. | |
| 7,141,072 B2 | 11/2006 | Geistlich et al. | |
| 7,147,846 B2 | 12/2006 | Anderson et al. | |
| 7,427,284 B2 | 9/2008 | Seedhom et al. | |
| 7,887,792 B2 | 2/2011 | Chancellor et al. | |
| 7,906,110 B2 | 3/2011 | Chancellor et al. | |
| 2002/0090389 A1 | 7/2002 | Humes et al. | |
| 2002/0155096 A1 | 10/2002 | Chancellor et al. | |
| 2003/0003085 A1* | 1/2003 | Kunkel et al. | 424/93.21 |
| 2004/0043008 A1 | 3/2004 | Vilquin et al. | |
| 2005/0048039 A1 | 3/2005 | Dreyfus et al. | |
| 2005/0220775 A1* | 10/2005 | Chancellor et al. | 424/93.21 |
| 2005/0265978 A1 | 12/2005 | Chancellor et al. | |
| 2006/0078993 A1 | 4/2006 | Phan et al. | |
| 2006/0280726 A1 | 12/2006 | Chancellor et al. | |
| 2007/0065416 A1 | 3/2007 | Chancellor et al. | |
| 2007/0065417 A1 | 3/2007 | Chancellor et al. | |
| 2008/0152627 A1 | 6/2008 | Chancellor et al. | |
| 2009/0010897 A1 | 1/2009 | Chancellor et al. | |
| 2009/0221644 A1 | 9/2009 | Bradley et al. | |
| 2011/0223139 A1 | 9/2011 | Chancellor et al. | |

FOREIGN PATENT DOCUMENTS

| | | |
|---|---|---|
| WO | WO-9618303 A1 | 6/1996 |
| WO | WO-9639035 A1 | 12/1996 |
| WO | WO-9836055 A1 | 8/1998 |
| WO | WO-9844142 A1 | 10/1998 |
| WO | WO-9854301 A2 | 12/1998 |
| WO | WO-9946366 A1 | 9/1999 |
| WO | WO-9947163 A2 | 9/1999 |
| WO | WO99/56785 A2 | 11/1999 |
| WO | WO-9956785 A2 | 11/1999 |
| WO | WO-9956786 A1 | 11/1999 |
| WO | 00/17322 A | 3/2000 |
| WO | 00/29552 A | 5/2000 |
| WO | WO-0119966 A2 | 3/2001 |
| WO | WO01/78754 A2 | 10/2001 |
| WO | WO02/067867 A2 | 9/2002 |
| WO | 2004096245 A2 | 11/2004 |
| WO | WO-2008076435 A1 | 6/2008 |
| WO | WO-2008086040 A1 | 7/2008 |
| WO | WO-2008153813 A2 | 12/2008 |
| WO | WO-2009045506 A2 | 4/2009 |
| WO | WO-2010022083 A2 | 2/2010 |

OTHER PUBLICATIONS

Norris et al. J. Bone joint Surg. 1988. 70-B: 530-3.*
A definition of "Urethra" retrieved from the Medterm website : http://www.medterms.com/script/main/art.asp?articlekey=5907&pf=3&page=1 on May 23, 2010.*
Mulcahy. (Semin. Urol. Oncol. Feb. 2000; 18: 71-5.*
Jiang et al. Eur. Urology, 2004; 43: 211-218.*
El-Galley et al. J. Urology 2001; 166:927-931.*
U.S. Appl. No. 09/302,896, filed Apr. 30, 1999, Chancellor et al.
U.S. Appl. No. 09/549,937, filed Apr. 14, 2000, Chancellor et al.
Acsadi et al., A differential efficiency of adenovirus-mediated in vivo gene transfer into skeletal muscle cells of different maturity. *Hum Mol Genet.* Apr. 1994;3(4):579-84.
Bayer, SA, Neuron production in the hippocampus and olfactory bulb of the adult rat brain: addition or replacement? *Ann N Y Acad Sci.* 1985;457:163-72.
Carlson and Nitti, Prevention and management of incontinence following radical prostatectomy. *Urol Clin North Am.* Aug. 2001;28(3):595-612. Review.
Faustman et al., Prevention of xenograft rejection by masking donor HLA class I antigens. *Science.* Jun. 21, 1991;252(5013):1700-2.
Kaplan et al., Neurogenesis in the 3-month-old rat visual cortex. *J Comp Neurol.* Jan. 10, 1981;195(2):323-38.
Pfister et al., Assessment of the intrinsic urethral sphincter component function in postprostatectomy urinary incontinence. *Neurourol Urodyn.* 2002;21(3):194-7.
Price et al., Lineage analysis in the vertebrate nervous system by retrovirus-mediated gene transfer. *Proc Natl Acad Sci U S A.* Jan. 1987;84(1):156-60.
Rippe et al., DNA-mediated gene transfer into adult rat hepatocytes in primary culture. *Mol Cell Biol.* Feb. 1990;10(2):689-95.
Sanes et al., Use of a recombinant retrovirus to study post-implantation cell lineage in mouse embryos. *EMBO J.* Dec. 1, 1986;5(12):3133-42.
Watt et al., Long term survival of allografted muscle precursor cells following a limited period of treatment with cyclosporin A. *Clin Exp Immunol.* Feb. 1984;55(2):419-26.
Abstract, JP2000287683, titled: "Skeletal muscle derived component useful for treating amyotrophic lateral sclerosis, is isolated from skeletal muscle cell homogenate using a series of centrifugation and column chromatography", 2 pages.
B.M. Deasy et al., 2002, "Mechanisms of Muscle Stem Cell Expansion with Cytokines", *Stem Cells*, 20:50-60.
Chancellor, et al. "Gene Therapy Strategies for Urological Dysfunction", *Trends in Molecular Medicine*, 7:301-306 (2001).
Chen, et al. "High-Efficiency Transformation of Mammalian Cells by Plasmid DNA", *Molecular and Cellular Biology*, 7:2745-2732 (1987).
Fechheimer, et al. Transfection of Mammalian Cells With Plasmid DNA by Scrape Loading and Sonication Loading, *Proc. Natl. Aca. Sci. USA*, 84:8463-8467 (1987).
Fraley, et al., "Entrapment of a Bacterial Plasmid in Phospholipid Vesicles: Potential for Gene Transfer", *Proc. Natl. Acad. Sci. USA*, 76:3348-3352 (1979).
Graham, et al., A New Technique for the Assay of Infectivity of Human Adenovirus 5 DNA, *Virology*, 52:456-467 (1973).
Harland, et al. "Translation of mRNA Injected Into *Xenopus* Oocytes is Specifically Inhibited by Antisense RNA", *The Journal of Cell Biology*, 101:1094-1099 (1985).
Huard, et al. "Muscle-Derived Cell-Mediated Ex Vivo Gene Therapy for Urological Dysfunction"; *Gene Therapy*, 9:1617-1626 (2002).
Potter, et al. Enchancer-Dependent Expression of Human K Immunoglobulin Genes Introduced Into Mouse Pre-B lymphocytes by Electroporation, *Proc. Natl. Acad. Sci. USA*, 81:7161-7165 (1984).
Qu-Petersen, et al. "Identification of a Novel Population of Muscle Stem Cells in Mice: Potential for Muscle Regeneration"; *Journal of Cell Biology*, 157:851-864 (2002).
Qu-Petersen, et al. "Muscle Derived Stem Cells Contribute to Blood Vessel and Peripheral Nerve Formation", *Molecular Biology of the Cell*, 12:366A-367A, (2001). Abstract 2013.
Sakai, et al. "The Use of Ex Vivo Gene Transfer Based on Muscle-Derived Stem Cells for Ardiovascular Medicine", *Trends in Cardiovascular Medicine 2002* United States, 12:115-120 (2002).
Shen, et al. Structural and Functional Healing of Critical-Size Segmental Bone Defects by Transduced Muscle-Derived Cells Expressing $BMP_4$, *J. Gene Med.*, 6:984-991 (2004).
Tirney, et al. "Nitric Oxide Synthase Gene Therapy for Erectile Dysfunction: Comparison of Plasmid, Adenovirus, and Adenovirus-Transduced Myoblast Vectors", *Molecular Urology*, 5:37-43 (2001).
Torrente, et al. "Intraarterial Injection of Muscle-Derived CD34+Sca-1+ Stem Cells Restores Dystrophin in Mdx Mice"; *Journal of Cell Biology*, 152:335-348 (2001).

(56) References Cited

OTHER PUBLICATIONS

Tur-Kaspa, et al. "Use of Elecroporation to Introduce Biologically Active Foreign Genes Into Primary Rat Hepatocytes", *Molecular and Cellular Biology*, 6:716-718 (1986).
Wu, et al. "Evidence for Targeted Gene Delivery to Hep G2 Hepatomoa Cells In Vitro", *Biochemistry*, 27:887-892 (1988).
Wu, et al. "Receptor-Mediated In Vitro Gene Transformation by a Soluble DNA Carrier System", *The Journal of Biological Chemistry*, 262:4429-4432 (1987).
Yang, et al. "In Vivo and In Vitro Gene transfer to Mammalian Somatic Cells by Particle Bombardment", *Proc. Natl. Acad. Sci. USA*, 87:9568-8572 (1990).
Young, et al. "Muscle-Based Gene Therapy and Tissue Engineering to Improve Bone Healing", 403s:s243-s251 (2002).
Chancellor et al., (2000), Neurourology and Urodynamics, 19(3):279-287.
Supplementary European Search Report, Appl. No. EP 02706457, Mailed on May 27, 2009.
Fukuda et al., (2000), Tanpakushita Kakusan Kouso (Protein, Nucleic Acid and Enzyme) 45(13), 2078-2084.
Ikada (2001), "Tissue Engineering—Toward Establishing of Basic Technology and Clinical Applications," Kagaku-Dojin Publishing Co., Inc. pp. 183-191.
Japanese Office Action, Application No. JP2002-567239, Date: Feb. 7, 2007 (with English Translation).
Pre-Appeal Examination Report, Appl. No. JP2002-567239, Date: Oct. 22, 2007 (with English Translation).
First Office Action, Appl. No. CN200480018035.2, Issued on Jul. 6, 2007.
Tirney S. et al., (2001), Mol. Urol. 5(1):37-43.
Qu-Peterson, Z. et al., (2003), Exp. Hematol. 31(7), Suppl. 1:133. (Abstract).
Written Opinion of the International Searching Authority, Appl. No. PCT/US2004/013115, Mailed on: Oct. 28, 2005.
European Examination Report, Appl. No. 04750822.1-2107, Mailed on Nov. 27, 2007.
Kaufman et al. (1988), PNAS, 85:9606-9610.
Office Action issued for U.S. Appl. No. 11/505,735, Mail Date: Sep. 9, 2009.
Ding et al., "Bone marrow stromal cells as a vehicle for gene transfer", Gene Therapy (1999), 6(9):1611-1616.
Gussoni et al., "Normal dystrophin transcripts detected in Duchenne muscular dystrophy patients after myoblast transplantation", Nature (1992), 356:435-438.
Seale et al., "A New Look at the Origin, Function, and 'Stem-Cell' Status of Muscle Satellite Cells", Developmental Biology (2000), 218:115-124.
Ziegler et al., "KDR Receptor: A Key Marker Defining Hematopoietic Stem Cells", Science (1999), 285:1533-1558.
Berjukow et al., "Membrane properties of single muscle cells of the rhabdosphincter of the male urethra", Prostate (2004), 58(3): 238-247.
Yokoyama et al., "Myoblast therapy for stress urinary incontinence and bladder dysfunction", World Journal of Urology (2000), 18(1):56-61.
Andersson et al. "Advances in the Pharmacological Control of the Bladder." *Exp. Physiol.* 84(1999):195-213.
Jancel et al. "Management of Uncomplicated Urinary Tract infections." *West J. Med.* 176(2002):51-55.
Rando et al. "Methods for Myoblast Transplantation." *Meth. Cell Biol.* 52(1998):261-272.
Abraham et al. "Evaluation of the Porcine Intestinal Collagen Layer as a Biomaterial," *J. Biomed. Mat. Res.* 51.3(2000):442-452.
Abrams et al. "The Standardisation of Terminology of Lower Urinary Tract Function: Report From the Standardisation Sub-Committee of the International Continence Society," *Neurol. Urodynam.* 21.2(2002):167-178.
Adachi et al. "Muscle Derived, Cell Based Ex Vivo Gene Therapy for Treatment of Full Thickness Articular Cartilage Defects." *J. Rheumatol.* 29.9(2002):1920-1930.
Alden et al. "In Vivo Endochondral Bone Formation Using a Bone Morphogenetic Protein 2 Adenoviral Vector." *Hum. Gene Ther.* 10(1999):2245-2253.
Anderson. "Human Gene Therapy." *Nature.* 382(1998):25-30.
Andrews et al. "Monoclonal Antibody 12-8 Recognizes a 115-kd Molecule Present on Both Unipotent and Multipotent Hematopoietic Colony-Forming Cells and Their Precursors." *Blood.* 67(1986):842-845.
Anwer et al. "Systemic Effect of Human Growth Hormone After Intramuscular Injection of a Single Dose of a Muscle-Specific Gene Medicine." *Hum. Gene Ther.* 9(1998):659-670.
Arcila et al. "Mass and Functional Capacity of Regenerating Muscle is Enhanced by Myoblast Transfer." *J. Neurobiol.* 33(1997):185-198.
Ashman. "The Biology of Stem Cell Factor and its Receptor C-Kit." *Int. J. Biochem. Cell Biol.* 31(1999):1037-1051.
Atkins et al. "Intracardiac Transplantation of Skeletal Myoblasts Yields Two Populations of Striated Cells In Situ," *Ann. Thorac. Surg.* 67(1999):124-129.
Atkins et al. "Myogenic Cell Transplantation Improves In Vivo Regional Performance in Infarcted Rabbit Myocardium." *J. Heart Lung Transplant.* 18(1999):1173-1180.
Auger et al. "Tissue-Engineered Human Skin Substitutes Developed from Collagen-Populated Hydrated Gels: Clinical and Fundamental Applications." *Med. Biol. Eng. Comput.* 36(1998):801-812.
Baltoyannis et al. "Submucosa of Canine Small Intestine as an Alternative Medium-Diameter Autogenous Arterial Graft." *Int. Angiol.* 19.3(2000):280-284.
Bandara et al. "Intraarticular Expression of Biologically Active Interleukin 1-Receptor-Antagonist Protein by ex vivo Gene Transfer." *PNAS.* 90(1993):10764-10768.
Baroffio et al. "Identification of Self-Renewing Myoblasts in the Progeny of Single Human Muscle Satellite Cells." *Differentiation.* 60(1996):47-57.
Barr et al. "Systemic Delivery of Recombinant Proteins by Genetically Modified Myoblasts." *Science.* 254(1991):1507-1509.
Bartynski et al. "Histopathologic Evaluation of Adipose Autografts in a Rabbit Ear Model." *Otolaryngol. Head Neck Surg.* 102(1990):314-321.
Beauchamp et al. "Dynamics of Myoblast Transplantation Reveal a Discrete Minority of Precursors with Stem Cell-Like Properties as the Myogenic Source." *J. Cell Biol.* 144(1999):1113-1122.
Beets-Tan et al. "Measurement of Anal Sphincter Muscles: Endoanal US, Endoanal MR Imaging, or Phased-Array MR Imaging? A Study With Healthy Volunteers." *Radiology.* 220(2001):81-89.
Berman et al. "Comparative Cost Analysis of Collagen Injection and Fascia Lata Sling Cystourethropexy for the Treatment of Type III Incontinence in Women." *J. Urol.* 157(1997):122-124.
Berthod et al. "Collagen Synthesis by Fibroblasts Cultured with a Collagen Sponge." *Biomat.* 14.10(1993):749-754.
Berthod et al. "In vitro reconstructed Skin Models for Wound Coverage in Deep Burns." *Brit. J. Dermatol.* 136(1997):809-816.
Blanton et al. "Isolation of Two Populations of Myoblasts From Porcine Skeletal Muscle." *Musc. Nerve.* 22(1999):43-50.
Boyce, "Cultured Skin Substitutes: A Review." *Tissue Eng.* 2.4(1996):255-266.
Cannon et al. "Improved Sphincter Contractility After Allogenic Muscle-Derived Progenitor Cell Injection Into the Denervated Rat Urethra." *Urol.* 62.5(2003):958-963.
Chajchir et al. "Fat Grafting Injection for Soft-Tissue Augmentation." *Plast. Reconstr. Surg.* 84(1989):921-935.
Civin et al. "Antigenic Analysis of Hematopoiesis." *J. Immunol.* 133.1(1984):157-165.
Dalle et al. "Improvement of Mouse β-thalassemia Upon Erythropoietin Delivery by Encapsulated Myoblasts." *Gene Ther.* 6(1999):157-161.
Dana et al. "Interleukin-1 Receptor Antagonist Suppresses Langerhans Cell Activity and Promotes Ocular Immune Privilege." *Invest. Ophthalmol. Vis. Sci.* 39(1998):70-77.
Day et al. "Myoblast-Mediated Gene Transfer to the Joint." *J. Ortho. Res.* 15(1997):894-903.

(56) References Cited

OTHER PUBLICATIONS

Deasy et al. "Gene Therapy and Tissue Engineering Based on Muscle-Derived Stem Cells." *Curr. Opin. Mol. Ther.* 4(2002):382-389.
Dhawan et al. "Systemic Delivery of Human Growth Hormone by Injection of Genetically Engineered Myoblasts." *Science.* 254(1992):1509-1512.
Dixon et al. "Recombinant Human Bone Morphogenetic Proteins-2 and -4 Induce Several Mesenchymal Phenotypes in Culture." *Wound Rep. Reg.* 4(1996):374-380.
Dominiv et al. "Bcl-2 Expression Identifies an Early Stage of Myogenesis and Promotes Clonal Expansion of Muscle Cells." *J. Cell Biol.* 142.2(1998):537-544.
Donovan et al. "The End of the Beginnings for Pluripotent Stem Cells." *Nature.* 414(2001):92-97.
Elia et al. "Genuine Stress Urinary Incontinence with Low Urethral Pressure: Five-Year Follow-Up After the Ball-Burch Procedure." *J. Repro. Med. Obst. Gynecologist.* 40.7(1995):503-506.
Ersek. "Transplantation of Purified Autologous Fat: A 3-Year Follow-Up is Disappointing." *Plast. Reconstr. Surg.* 87(1991):219-228.
Ferrari et al. "Muscle Regeneration by Bone Marrow Myogenic Progenitors." *Science.* 279(1998):1528-1530.
Fina et al. "Expression of the CD34 Gene in Vascular Endothelial Cells." *Blood.* 75.12(1990):2417-2426.
Friedmann. "Principles for Human Gene Therapy Studies." *Science.* 287.5461(2001):2163-2165.
Game et al. "Rejection Mechanisms in Transplantation." *Wien Klin Wochenschr.* 113(2001):823-838.
Gao et al. "The Dynamic in vivo Distribution of Bone Marrow-Derived Mesenchymal Stem Cells after Infusion." *Cells Tissues Organs.* 169(2001):12-20.
Garban et al. "Cloning of Rat and Human Inducible Penile Nitric Oxide Synthase." *Biol. Reprod.* 56.4(1997):954-963.
Germain et al. "Tissue Engineering of the Vascular System: From Capillaries to Larger Blood Vessels." *Med. Biol. Eng. Comput.* 38(2000):232-240.
Gibson et al. "Dermal Fibroblasts Converts to a Myogenic Lineage in mdx Mouse Muscle." *J. Cell Sci.* 108(1995):207-214.
Grinnell. "Trophic Interaction Between Nerve and Muscle." *Myology.* Engel et al., eds. New York: McGraw-Hill, Inc. 2(1994):303-332.
Gros et al. "Insulin Production by Engineered Muscle Cells." *Hum. Gene Ther.* 10(1999):1207-1217.
Gross et al. "Muscle Precursor Cells Injected Into Irradiated mdx Mouse Muscle Persist After Serial Injury." *Muscle Nerve.* 22.2(1999):174-185.
Gussoni et al. "Dystrophin Expression in the mdx Mouse Restored by Stem Cell Transplantation." *Nature.* 401(1999):390-394.
Hansborough et al. "Evaluation of a Biodegradable Matrix Containing Cultured Human Fibroblasts as a Dermal Replacement Beneath Meshed Skin Grafts on Athymic Mice." *Surg.* 111.1(1992):438-446.
Hortelano et al. "Persistent Delivery of Factor IX in Mice: Gene Therapy for Hemophilia Using Implantable Microcapsules." *Hum. Gene Ther.* 10(1999):1281-1288.
Huard et al. "Differentiation of Primary Myoblast Injection Into the Lower Urinary Tract; Creation of Detrusor Cellular Myoplasty." *J. Urol.* 161.4S(1999):66. (Abstract #248).
Huard et al. "High Efficiency of Muscle Regeneration After Human Myoblast Clone Transplantation in SCID Mice." *J. Clin. Invest.* 93(1994):586-599.
Huard et al. "Human Myoblast Transplantation in Immunodeficient and Immunosuppressed Mice: Evidence of Rejection." *Muscle Nerve.* 17(1994):224-234.
Huard et al. "Human Myoblast Transplantation: Preliminary Results of 4 Cases." *Muscle Nerve.* 15(1992):550-560.
Huard et al. "Myoblast Injection Into the Bladder Wall: A Possible Method of Modulating Detrusor Contractility and Cell-Medicated Gene Therapy for Bladder Dysfunction." *J. Urol.* 159.S5(1998):16. (Abstract #62).
Huard et al. "Nitric Oxide Synthases (NOS) Gene Therapy for Erectile Dysfunction; COMparison Between Plasmid, Adenovirus and Adenovirus Transduced Myoblast Vectors." *J. Urol.* 159(1998):90. (Abstract #342).
Huard et al. "The Route of Administration is a Major Determinant of the Transduction Efficiency of Rat Tissues by Adenoviral Recombinants." *Gene Ther.* 2(1995):107-115.
Hörl et al. "Technique for Liposuction Fat Reimplantation and Long-Term Volume Evaluation by Magnetic Resonance Imaging." *Ann. Plast. Surg.* 26(1991):248-258.
Irintchev et al. "Ectopic Skeletal Muscles Derived from Myoblasts Implanted Under the Skin." *J. Cell Sci.* 111(1998):3287-3297.
Irintchev et al. "Expression Pattern of M-Cadherin in Normal, Denervated, and Regenerating Mouse Muscles." *Dev. Dynam.* 199(1994):326-337.
Jackson et al. "Hematopoietic Potential of Stem Cells Isolated from Murine Skeletal Muscle." *PNAS.* 96.25(1999):14482-14486.
Jankowski et al. "Flow Cytometric Characterization of Myogenic Cell Populations Obtained Via the Preplate Technique: Potential for Rapid Isolation of Muscle-Derived Stem Cells." *Hum. Gene Ther.* 12(2001):619-628.
Jiao et al. "Intracerebral Transplants of Primary Muscle Cells: A Potential 'Platform' for Transgene Expression in the Brain." *Brain Res.* 575(1992):143-147.
Jung et al. "Urethral Afferent Nerve Activity Affects the Micturition Reflex; Implication of the Relationship Between Stress Incontinence and Detrusor Instability." *J. Urol.* 162.1(1999):204-212.
Karpati et al. "Myoblast Transfer in Duchenne Muscular Dystrophy." *Ann. Neurol.* 34(1993):8-17.
Kasemjikwattana et al. "Development of Approaches to Improve the Healing Following Muscle Contusion." *Cell Transplant.* 7.6(1998):585-598.
Katagiri et al. "Bone Morphogenetic Protein-2 Converts the Differentiation Pathway of C2C12 Myoblasts into the Osteoblast Lineage." *J. Cell Biol.* 127(1994):1755-1766.
Koretzky et al. "Role of the CD45 Tyrosine Phosphatase in Signal Transduction in the Immune System." *FASEB J.* 7(1993):420-426.
Kropp et al. "Bioengineering Organs Using Small Intestinal Submucosa Scaffolds: In Vivo Tissue Engineering Technology." *J. Endourol.* 14.1(2000):59-62.
Kropp et al. "Regenerative Urinary Bladder Augmentation Using Small Intestinal Submucosa: Urodynamic and Histopathologic Assessment in Long-Term Canine Bladder Augmentations." *J. Urol.* 155(1996):2098-2104.
Kuby. "Transplantation Immunology." *Immunology* New York: W.H. Freeman and Co. 2(1994):559-560.
Kühl et al. "Role of Laminin and Fibronectin in Selecting Myogenic Versus Fibrogenic Cells from Skeletal Muscle Cells in Vitro." *Dev. Biol.* 117(1986):628-635.
Langer et al. "Tissue Engineering." *Science.* (260)(1993):920-926.
Ledley. "Pharmaceutical Approach to Somatic Gene Therapy." *Pharma. Res.* 13.11(1996):1595-1614.
Lee et al. "Clonal Isolation of Muscle-Derived Cells Capable of Enhancing Muscle Regeneration and Bone Healing." *J. Cell Biol.* 150.5(2000):1085-1099.
Lee et al. "New Functional Sphincter Formation After Allogenic Muscle Derived Stem Cell Injection Into Denervated Rat Urethral Sphincter." *J. Urol.* 165.Supplement(2001):254. (Abstract #1033).
Lee et al. "The Effects of Periurethral Muscle-Derived Stem Cell Injection on Leak Point Pressure in a Rat Model of Stress Urinary Incontinence." *Int. Urogynecol. J.* 14(2003):31-37.
Lipton et al. "Developmental Fate of Skeletal Muscle Satellite Cells." *Science.* 205(1979):1292-1294.
Lucas et al. "A Population of Cells Resident Within Embryonic and Newborn Rat Skeletal Muscle is Capable of Differentiating into Multiple Mesodermal Phenotypes." *Wound Rep. Regen.* 3.4(1995):449-460.
Lucas et al. "Effect of Rat Mesenchymal Stem Cells on Development of Abdominal Adhesions After Surgery." *J. Surg. Res.* 6.2(1996):229-232.
Lynch et al. "Long-Term Expression of Human Adenosine Deaminase in Vascular Smooth Muscle Cells of Rats: A Model for Gene Therapy." *PNAS.* 89(1992):1138-1142.

(56) References Cited

OTHER PUBLICATIONS

Madeiro et al. "Effects of the Association of Androgen/Estrogen on the Bladder and Urethra of Castrated Rats." *Clin. Exp. Obstet. Gynecol.* 29.2(2002):117-120.
Mak et al. "Injectable Filler Materials for Soft-Tissue Augmentation." *Otolaryngol. Clin. North Am.* 27.1(1994):211-222.
Martini et al. "Integration With Other Systems." *Fundamentals of Anatomy and Physiology*. Englewood Cliffs, New Jersey: Prentice Hall. (1995):315-318.
Miller et al. "Seeking Muscle Stem Cells." *Curr. Top. Dev. Biol.* 43(1999):191-219.
Minuth et al. "Tissue Engineering: Generation of Differentiated Artificial Tissues for Biomedical Applications." *Cell Tissue Res.* 291(1998):1-11.
Moisset et al. "Expression of Human Dystrophin Following the Transplantation of Genetically Modified mdx Myoblasts." *Gene Ther.* 5(1998):1340-1346.
Moisset et al. "Successful Transplantation of Genetically Corrected DMD Myoblasts Following ex Vivo Transduction with the Dystrophin Minigene." *Biochem. Biophys. Res. Commun.* 247(1998):94-99.
Morgan et al. "Partial Correction of an Inherited Biochemical Defect of Skeletal Muscle by Grafts of Normal Muscle Precursor Cells." *J. Neurol. Sci.* 86(1988):137-147.
Murry et al. "Skeletal Myoblast Transplantation for Repair of Myocardial Necrosis." *J. Clin. Invest.* 98(1996):2512-2523.
Musgrave et al. "Muscle-Based Tissue Engineering for the Musculoskeletal System." *Gene Ther. Mol. Biol.* 3(1998):1-15.
Naughton et al. "Human-Based Tissue Engineered Implants for Plastic and Reconstructive Surgery." *Clin. Plastic Surg.* 26.4(1999):579-586.
Newman et al. "Stress Urinary Incontinence in Women." *Am. J. Nurs.* 103.8(2003):46-55.
Nguyen et al. "Comparative Study of Survival of Autologous Adipose Tissue Taken and Transplanted by Different Techniques." *Plast. Reconstr. Surg.* 85.3(1990):378-389.
Nurcombe et al. "Motoneurone Survival and Neuritic Outgrowth Promoted by Different Cell Types in Embryonic Muscles." *Dev. Brain Res.* 21(1985):49-60.
Odorico et al. "Multilineage Differentiation from Human Embryonic Stem Cell Lines." *Stem Cells.* 19(2001):193-204.
Osawa et al. "In Vivo Self-Renewal of c-Kit+ Sca-1+ Lin low/- Hemopoietic Stem Cells." *J. Immunol.* 156(1996):3207-3214.
Partridge et al. "Conversion of mdx Myofibres From Dystrophin-Negative to -Positive by Injection of Normal Myoblasts." *Nature.* 337(1989):176-179.
Partridge et al. "Evidence of Fusion Between Host and Donor Myoblasts in Skeletal Muscle Grafts." *Nature.* 273(1978):306-308.
Partridge et al. "Myoblast-Based Gene Therapies." *Brit. Med. Bullet.* 51.1(1995):123-137.
Payne et al. "Muscle-Derived Stem Cells Express a Cardiac Phenotype Upon Transplantation into the Dystrophic Murine Heart." *Amer. Heart Assoc. Conf. Mol. Mechan. Growth Death Regen Myocard.* (2003)9. (Abstract #P42).
Pittenger et al. "Multilineage Potential of Adult Human Mesenchymal Stem Cells." *Science,* 284(1999):143-147.
Platt et al. "Knocking Out Xenograft Rejection." *Nat. Biotech.* 20.3(2002):231-232.
Qu et al. "Development of Approaches to Improve Cell Survival in Myoblast Transfer Therapy." *J. Cell Biol.* 142.5(1998):1257-1267.
Qu et al. "Identification of Muscle-Derived Stem Cells." *Mol. Biol. Cell.* 10(1999):246a.
Rando et al. "Primary Mouse Myoblast Purification, Characterization, and Transplantation for Cell-Mediated Gene Therapy." *J. Cell Biol.* 125.6(1994):1275-1287.
Richler et al. "The in Vitro Cultivation and Differentiation Capacities of Myogenic Cell Lines." *Dev. Biol.* 23(1970):1-22.

Roman et al. "Circulating Human or Canine Factor IX from Retrovirally Transduced Primary Myoblasts and Established Myoblast Cell Lines Grafted into Murine Skeletal Muscle." *Somat. Cell. Mol. Genet.* 18(1992):247-258.
Rosenberg et al. "Gene Therapist, Heal Thyself." *Science.* 287(2000):1751.
Régulier et al. "Continuous Delivery of Human and Mouse Erythropoietin in Mice by Genetically Engineered Polymer Encapsulated Myoblasts." *Gene Ther.* 5(1998):1014-1022.
Schäfer et al. "Anatomy of the Anal Sphincters." *Dis. Colon Rectum.* 37.8(1994):777-781. (Abstract Only).
Shafik. "Pelvic Double-Sphincter Control Complex." *Urol.* 23.6(1984):611-618.
Shapiro et al. "Novel Alginate Sponges for Cell Culture and Transplantation." *Biomat.* 18.8(1997):583-590.
Simmons et al. "CD34 Expression by Stromal Precursors in Normal Human Adult Bone Marrow." *Blood.* 78(1991):2848-2853.
Smith et al. "Stable Integration of an mdx Skeletal Muscle Cell Line Into Dystrophic (mdx) Skeletal Muscle: Evidence for Stem Cell Status." *Cell Growth Differ.* 8.8(1997):927-934.
Somogyi et al. "A Precise, Localized Bladder Injury Model to Investigate the Effect of Myoblast Injection on Bladder Contractility." *J. Urol.* 161.S4(1999):43. (Abstract #158).
Spindler et al. "Regional Mitogenic Response of the Meniscus to Platelet-Derived Growth Factor (PDGF-AB)." *J. Ortho. Res.* 13(1995):201-207.
Tirney et al. "Myoblast Periurethral Injection for the Treatment of Stress Urinary Incontinence." *J. Urol.* 159.S5(1998):327. (Abstract #1256).
Tokunaka et al. "Coexistence of Fast and Slow Myosin Isozymes in Human External Urethral Sphincter." *J. Urol.* 138.3(1987):659-662.
Tremblay et al. "Myoblast Transplantation: A Brief Review of the Problems and of Some Solutions." *Basic Appl. Myol.* 7.3-4(1997):221-230.
Tremblay et al. "Results of Triple Blind Clinical Study of Myoblast Transplantations Without Immunosuppressive Treatment in Young Boys with Duchenne Muscular Dystrophy." *Cell Transplant.* 2(1993):99-112.
Tzeng et al. "Vascular Inducible Nitric Oxide Synthase Gene Therapy: Requirement for Guanosine Triphosphate Cyclohydrolase I." *Surg.* 120.2(1996):315-321.
Van de Rijn et al. "Mouse Hematopoietic Stem-Cell Antigen Sca-1 is a Member of the Ly-6 Antigen Family." *PNAS.* 86(1989):4634-4638.
van Wachem et al. "Myoblast Seeding in a Collagen Matrix Evaluated in vitro." *J. Biomed. Mat. Res.* 30(1996):353-360.
Vandenburgh et al. "Tissue-Engineered Skeletal Muscle Organoids for Reversible Gene Therapy." *Hum. Gene Ther.* 7(1996):2195-2200.
Verma. "Gene Therapy: Beyond 2000." *Mol. Ther.* 1(2000):493.
Wang et al. "Persistent Systemic Production of Human Factor IX in Mice by Skeletal Myoblast-Mediated Gene Transfer: Feasibility of Repeat Application to Obtain Therapeutic Levels." *Blood.* 90(1997):1075-1082.
Watt et al. "Out of Eden: Stem Cells and Their Niches." *Science.* 287(2000):1427-1430.
Webster et al. "Isolation of Human Myoblasts with the Fluorscence-Activated Cell Sorter." *Exp. Cell Res.* 174(1988):252-265.
Williams et al. "Cell Isolated from Adult Human Skeletal Muscle Capable of Differentiating into Multiple Mesodermal Phenotypes." *Am. Surg.* 65.1(1991):22-26.
Yaffe et al. "Retention of Differentiation Potentialities During Prolonged Cultivation of Myogenic Cells." *PNAS.* 61(1968):477-483.
Yamanishi et al. "Identification of β-Adrenoceptor Subtypes in Lower Urinary Tract of the Female Pig." *J. Urol.* 168(2002):2706-2710.
Yao et al. "Primary Myoblast-Mediated Gene Transfer: Persistent Expression of Human Factor IX in Mice." *Gene Ther.* 1(1994):99-107.
Ye et al. "Tissue Engineering in Cardiovascular Surgery: New Approach to Develop Completely Human Autologous Tissue." *Eur. J. Cardio-Thorac. Surg.* 17(2000):449-454.

(56) References Cited

OTHER PUBLICATIONS

Yokoyama et al. "Autologous Primary Muscle-Derived Cells Transfer into the Lower Urinary Tract." *Tissue Engin.* 7.4(2001):395-404.
Yokoyama et al. "Gene Therapy as a Potential Treatment for BPH: Injection of Myoblast-Adenovirus Transfected with Human Inducible Nitric Oxide Synthase (iNOS) Into the Proximal Urethra." *J. Urol.* 161.S4(1999):305. (Abstract #1775).
Yokoyama et al. "Muscle-Derived Cell Transplantation and Differentiation Into Lower Urinary Tract Smooth Muscle." *Urol.* 57.4(2001):826-831.
Yokoyama et al. "Primary Myoblast Injection Into the Urethra and Bladder as a Potential Treatment of Stress Urinary Incontinence and Impaired Detrusor Contractility; Long Term Survival Without Significant Cytotoxicity." *J. Urol.* 161.S4(1999):307. (Abstract #1182).
Yoshida et al. "Cell Heterogeneity Upon Myogenic Differentiation: Down-Regulation of MyoD and Myf-5 Generates 'Reserve Cells.'" *J. Cell Sci.* 111(1998):769-779.
Young et al. "Human Reserve Pluripotent Mesenchymal Stem Cells are Present in the Connective Tissues of Skeletal Muscle and Dermis Derived from Fetal, Adult, and Geriatric Donors." *Anat. Rec.* 264.1(2001):51-62.
Young et al. "Mesenchymal Stem Cells Reside Within the Connective Tissues of Many Organs." *Dev. Dynam.* 202(1995):137-144.
Young et al. "Pluripotent Mesenchymal Stem Cells Reside Within Avian Connective Tissue Matrices." *In Vitro Cell. Dev. Biol.* 29A(1993):723-736.
Young et al. "Use of Mesenchymal Stem Cells in a Collagen Matrix for Achilles Tendon Repair." *J. Orthop. Res.* 16.4(1998):406-413.
Zhang et al. "Conculture of Bladder Urothelial and Smooth Muscles Cells on Small Intestinal Submucosa: Potential Applications for Tissue Engineering Technology." *J. Urol.* 164(2000):928-935.
Zheng et al. "Multi Potency of Myo-Endothelial Clones Isolated From Adult Human Skeletal Muscle." *Orthopaedic Res. Soc.* 53rd Annual Meeting (Feb. 12-14, 2007), Paper #0421.
Yokoyama et al., (2001). "Persistence and Survival of Autologous Muscle Derived Cells Versus Bovine Collagen as Potential Treatment of Stress Urinary Incontinence", J. Urology, 165:271-276.

\* cited by examiner ical decoration omitted>

MUSCLE-DERIVED CELLS (MDCS) FOR PROMOTING AND ENHANCING NERVE REPAIR AND REGENERATION

The United States Government may have certain rights in the present invention pursuant to Research Grant NIH 1P01 AR45925-01 from the National Institutes of Health.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

The present invention generally relates to the use of muscle-derived cells, preferably obtained from skeletal muscle, called MDCs herein, in promoting and enhancing the regeneration and repair of nerve cells and neuronal tissue. The invention further relates to MDCs for use in methods for repairing nerve tissue, particularly in the peripheral nervous system, and their ability to contribute to the development of neuronal tissue. Such methods are useful for the treatment of nervous system disorders and to alleviate, abate, ameliorate, or eliminate the symptoms of neurological or neurodegenerative diseases in animals, including humans, in both the central and peripheral nervous systems.

BACKGROUND OF THE INVENTION

The nervous system serves as a communication network between widely separated parts of the body and works rapidly to control reactions to stimuli, to process information and to produce complex patterns of signals that govern complex behaviors.

The vertebrate, e.g., mammalian, nervous system consists of the central nervous system (CNS), comprising the brain and spinal cord, which is linked by nerves (also referred to as nerve cells, neurons, or neuronal cells) to many peripheral structures, for example, sensory organs, muscles and glands. The CNS is also connected to peripheral nerve cell clusters, called ganglia, which play a role in communication between the peripheral and central nervous systems. Although the patterns of neural connections differ widely among different species, the properties of individual neurons (or nerve cells) are largely the same among animal nervous systems. The mature vertebrate, e.g., mammalian, central nervous system is made up of neurons, and glial cells, e.g., astrocytes and oligodendrocytes. The nerve cells, ganglia and sense organs comprise the peripheral nervous system.

The nervous system comprises large numbers of cells, which are highly specialized, yet which interact together to perform essential tasks and functions associated with their location in the system. For example, the neuromuscular junction, forming the junction between nerve cells and skeletal muscle, is composed of three cell types: a muscle cell, a nerve cell and a Schwann cell. Each has a very different roll as described below, yet they work together to allow muscle stimulation and contraction. The muscle cell is a specialized cell of contraction. Its cytoplasm is full of organized arrays of protein filaments, including vast numbers of actin filaments. Many mitochondria are also interspersed among the protein filaments and supply ATP to fuel the contractile apparatus.

The nerve cell of the neuromuscular junction stimulates the muscle cell to contract, conveying an excitatory signal to the muscle from the brain or spinal cord. The nerve cell is extremely elongated; its main body, containing the nucleus, can lie a meter or more from the junction of the muscle. Consequently, the cytoskeleton of a nerve cell is well developed so as to be able to maintain the unusual shape of the cell, and to transport materials efficiently from one end of the cell to the other through long nerve cell "processes". The plasma membrane of the nerve cell contains ion pump and channel proteins that have been exploited by the nerve cells so that electrical signals or pulses in the form of action potentials can propagate in a fraction of a second from one end of the cell to the other, thereby conveying a signal for action.

The last cell of the neuromuscular junction is the Schwann cell. Schwann cells are specialized to be mass producers of plasma membrane that wraps around the elongated portion of the nerve cell. Schwann cells in the peripheral nervous system form myelin and lay down many layers of membrane to form an insulating myelin sheath around the nerve cell process (called axons).

The generation of new nerve cells, known as the process of neurogenesis, is typically completed early in the post-natal period of life in vertebrate mammals. By the late post-natal period of mammalian development, the CNS contains a full complement of the various types of nerve cells. Most adult mammals, such as human and non-human primates, are unable to produce new nerve cells, which leads to serious problems when injury or disease causes damage to, or death of, neuronal cells and tissue that cannot be replaced.

Disorders and diseases of the CNS include a variety of adverse conditions, such as neurodegenerative diseases, for example, Parkinson's disease and its associated dyskinesias; Alzheimer's disease; multiple sclerosis (MS), amyolotrophic lateral sclerosis (ALS), Huntington's disease; acute brain injury, for example, stroke, cerebral palsy, head injury; and other CNS dysfunctions, for example, epilepsy, depression, schizophrenia, and palsies. Such disorders and diseases are becoming increasingly apparent in view of the growth of the aging population, which today enjoys a greater life-span and longevity. Many of the foregoing diseases, particularly of the elderly, have been associated with the degeneration of, or abnormalities in, cells in particular areas of the CNS, such that the cells of the CNS or the periphery cannot perform their normal functions. The abnormal functioning of existing nerve cells, rather than complete loss of the cells, encompasses a large area of CNS disorders, diseases and dysfunctions. Abnormalities in neuronal cells can derive from the inappropriate firing of neurons, or the abnormal synthesis, processing, and/or release of neurotransmitters. Other diseases and disorders involving damaged or dysfunctional nerve cells and tissue include traumas or tissue insults or various sorts, e.g., blunt trauma, burns, back injuries, muscle injuries, erectile dysfunction and the like.

The degeneration of the basal ganglia in the brain can result in the onset of diseases having a number of cognitive and motor symptoms, depending on the location in the body. The basal ganglia comprises many separate regions, including the striatum, i.e., containing the caudate and putamen, the globus pallidus, the substantia nigra, the substantia innomiante, the ventral pallidum, the nucleus basalis of Meynert (which sends cholinergic projections to the cerebral cortex), the ventral tegmental area and the subthalamic nucleus. Various regions of the basal ganglia are found to have undergone degeneration, or localized degeneration, in particular diseases, such as Alzheimer's disease or motor dysfunctions and diseases, such as Huntington's chorea or Parkinson's disease.

Demyelinating diseases include pathologies of neuronal cells in the CNS and peripheral nervous system yielding improper conductance of signals within and between these systems. Myelin, the cellular sheath, serves to improve various electrochemical properties of axons and axonal processes that are surrounded by myelin, which also provides trophic support to the neuron. In the CNS, oligodendrocytes produce myelin, while Schwann cells produce this insulating material in the peripheral nervous system. The demyelinating disease Multiple Sclerosis (MS) and muscular dystrophy are types of diseases involving neurological impairment for which treatments are needed.

The need for new treatments and approaches for alleviating and overcoming CNS and peripheral nervous system neurodegenerative disorders and diseases is an ongoing one. Although various treatments have been developed, there are drawbacks which detract from prolonged use of many treatments because of a lack of sustained long term effect, complications associated with use, and/or a lack of ease and effectiveness of treatment over time. For example, neuroleptics and pharmaceutical agents have been used to treat CNS disorders with limited success. Problems ensue due to the limited ability of the pharmaceutical agents to cross the blood-brain barrier. The development of tolerance to drugs also occurs, especially when drugs are administered to patients over time, thereby limiting effectiveness of treatment. Countermeasures, such as increasing the amount of drug administered to achieve heightened effectiveness, can result in adverse side effects, such as, for example, tardive dyskinesia, shaking, and other involuntary movements. Neurotransplantation using grafting techniques has been tried, yet the cell types involved are often not able to differentiate into the proper neuronal phenotype, or they are short-lived following introduction into a host or recipient.

Both the low turnover of cells in the mammalian CNS and the inability of adult mammals to regenerate or replace neuronal cells following injury or disease, e.g., neurodegenerative disease, support the notion that the adult CNS does not contain, and cannot generate, neural stem cells, or early cells, that exhibit self-renewal, thereby generating more progeny neuronal cells. In general, several hallmarks that are typical of stem cells are that they can renew and maintain themselves, proliferate, generate many differentiated functional progeny, and regenerate tissue after injury or disease. Stem cells are thus typically pluripotent and function to replace cell loss following natural or induced cell death, disease, injury, or dysfunction. The generation of new CNS cells after injury or death is rare among mammalian species (Kaplan, 1981, *J. Comp. Neurol.,* 195:323; Bayer, 1985, *Ann. New York Acad. Sci.,* 457:163; U.S. Pat. No. 6,497, 872), further supporting the theory that the adult mammalian CNS does not contain pluri- or multi-potent neural stem cells which might serve to replace neuronal cells lost as a result of injury or disease.

In terms of the treatment of neurodegenerative diseases and nerve injuries of various types, there is a need for a reproducible and effective source of cells that are available in amounts needed for introduction or transplantation into a host in need of treatment. Reports of various cell types for use in treating injuries and diseases of the nervous system include spontaneously occurring cell lines, immortalized cell lines, primary neural cell cultures, cells as described in U.S. Pat. No. 5,082,670 to Gage et al., who used fibroblasts genetically modified to express tyrosine hydroxylase, thus allowing them to produce dopamine to treat Parkinson's disease after implantation, and cells as described in U.S. Pat. No. 6,497,872 to Weiss et al., which discloses neuronal stem cells isolated from fetal or adult neural tissue, treated with growth factor, and allowed to differentiate into neural cell types prior to transplantation into a host.

Thus, there is a clear and ample need for the employment of reliable cell types having the ability to support nerve cell growth and survival; to promote or enhance the regeneration of injured nerves; and to promote or enhance innervation of transplanted or grafted tissues for the treatment of a variety of nervous system-related injuries, damage, diseases, disorders, or dysfunctions. There is further need for cells that can be locally or systemically administered into a recipient tissue to repair, ameliorate, eliminate, or recover function associated with peripheral nerve degeneration or inflammation, for example. The invention as described herein addresses such needs in the art of neuropathology and nerve cell and tissue disease treatment, improvement, repair and recovery.

SUMMARY OF THE INVENTION

One aspect of the present invention provides methods of supporting the regeneration of nerve cells of the nervous system, particularly, peripheral nerves, utilizing muscle-derived cells (referred to herein as MDCs), preferably isolated from skeletal muscle. MDCs, a population of early muscle-derived cells including myoblasts, have the ability to incorporate into areas of regenerating nerves, particularly peripheral nerves, and promote or enhance treatment and/or repair of damaged nerve tissue. In addition, MDCs display the potential for repairing both peripheral nerves and skeletal myofibers in nerve-injured muscle compared to non-injured muscle. As used herein, the term "peripheral nerves" refers to all nerve tissue exclusive of the central nervous system, including the spinal nerves, cranial nerves, autonomic nerves, dorsal root ganglia, and autonomic ganglia. In some aspects, neurotrophic factors, which are up-regulated by neural injury, can improve treatments using MDCs injected into diseased, damaged, injured, or dysfunctional tissues. MDCs also can contribute to the repair of injured tissues, for example, nerve and muscle tissue, in response to local environmental signals (e.g., growth and differentiation factors) from damaged tissues and organs. In some aspects, myoblast MDCs are enriched by successive culture platings to remove non-muscle cells and fibroblasts and the enriched, cultured myoblast MDCs are utilized in the methods described herein.

Another aspect of the present invention provides a reliable source of MDCs that are capable of proliferating and maintaining sustained viability following introduction or transplantation into an area where nerve damage, injury, or disease has occurred. In accordance with this aspect, methods of utilizing MDCs are provided to enrich in a cell population that survives where needed, so as to treat, ameliorate, or eliminate injury, disease, or damage in nerves and nerve tissue. The MDC source is suitable for neuronal cell and/or tissue repair and regeneration in autografts. In some instances, MDCs may be suitable for use in allografts and xenografts, without a concern for tumor formation or rejection, as these cells may enjoy an immune privilege that allows them to escape surveillance leading to rejection, such as graft-versus-host rejection, by host immune systems.

In another aspect, the present invention provides a method of supporting the survival, regeneration and repair of nerve cells and tissue, comprising introducing MDCs in or around a site of injured, damaged, diseased, or dysfunctional tissue to support the innervation (or re-innervation), regeneration and repair of nerve cells in the tissue or tissue area undergoing MDC treatment. The MDCs comprise an enriched population of viable, non-fibroblast, desmin-positive, myoblastic, early muscle-derived cells. MDCs for use in the method can be enriched by performing at least two successive platings in tissue culture containers to remove fibroblast cells, non-muscle and non-myoblast cells. The MDCs can be autologous to the tissue into which they are introduced.

In another of its aspects, the present invention provides the use of MDCs to promote and/or enhance neuronal survival and regeneration in transplanted tissues or organs and to stimulate the innervation of transplanted tissues or organs by nerve fibers of the host tissue or organ. In accordance with this aspect, MDCs are administered along or near the border between transplanted and host tissues, either separately or in conjunction with a physiologically acceptable carrier, excipient, or diluent. Thus, according to such methods, MDCs can prevent or retard the degeneration of peripheral cutaneous axons that have been damaged, for example, by severe burn injuries, or insult, or blunt trauma to a tissue or organ, thereby enhancing the capacity of these axons to innervate autologous skin grafts. In a related aspect, the MDCs carry one or more heterologous polynucleotides encoding one or more neurotrophic or growth factors which are expressed in vivo by the MDCs and which contribute to the neuroprotective and ameliorative properties of the MDCs used in the methods.

In a further aspect of the present invention, MDCs are employed to promote and/or enhance innervation or re-innervation of severed or partially severed tissues or limbs subject to surgical reattachment. According to this aspect of the invention, MDCs are applied at the site of injury, e.g., at the distal site, the proximal site, or both, and are administered either separately or in combination with a physiologically acceptable carrier, excipient, or diluent. The neuroprotective properties of the MDCs promote the innervation or re-innervation of the reattached tissue and the restoration of functional connections between severed axons. The MDCs in accordance with this aspect of the invention can also be engineered to express one or more neurotrophic or growth factors, which, upon expression in vivo, can enhance the neuroprotective and ameliorative effects of the MDCs used in the method.

Yet another aspect of the present invention provides MDCs that can be employed in an in vitro culture system for use in the testing or screening of drugs, compounds, agents, molecules, and the like, which are potential neurologic therapeutics, to determine their effectiveness in allowing MDCs to support the growth and/or regeneration of nerve cells, and/or to affect the behavior, growth, viability, activity, or function of the neuronal cells in injured, damaged, diseased or dysfunctional neuronal tissue. In accordance with this aspect, a method is provided for the screening of such potential neurologic therapeutics and pharmaceuticals using the MDCs, preferably treated with one or more growth or trophic factors, such as NGF, ciliary neurotrophic factor (CNTF), neurotrophin, or other factors, for example, and cultured in vitro. Alternatively, if the cultures of MDCs are not pre-treated with growth or trophic factors, these cultures can be used to evaluate or test for the ability of a candidate or test compound, substance, drug, pharmaceutical, or other agent to affect, e.g., stimulate, induce, etc., the ability of MDCs to support innervation and/or nerve cell growth and/or regeneration. Such test methods can involve treating a culture of MDCs with a test substance; introducing the treated MDCs into a site of nerve tissue injury, disease, or damage; and comparing the ability of the treated MDCs to support innervation or nerve cell growth in a recipient having nerve tissue disease, damage, or injury relative to the ability of non-treated MDCs to support innervation or nerve cell growth in the recipient. Appropriate controls, e.g., non-treated cultures, are encompassed by the testing and screening methods.

A further aspect of the present invention provides a method for introducing or transplanting MDCs into a host having a neurodegenerative disease, disorder, injury, or dysfunction, in which the method comprises introducing into host tissue MDCs or a physiologically acceptable composition thereof. MDCs can be isolated from skeletal muscle as an enriched end population of early muscle-derived cells, such as myoblasts, by a series of plating and culturing steps. The culturing enrichment provides an end population of MDCs for use in the methods described herein. The MDCs are viable, non-fibroblast, desmin-positive cells that can form muscle fibers (myofibers) and can also promote, enhance, or ameliorate repair of nerve innervation and nerve cell and tissue damage. During the successive platings of cells into new containers, MDCs (including myoblasts, satellite cells, and early muscle-derived cells, e.g., muscle stem cells) are enriched and separated from non-MDC types, e.g., fibroblasts and adipocytes, endothelial cells, and connective tissue cells. The successive platings can be carried out for about 3-7 days, or 4-6 days, or 3-5 days, until non-fibroblast MDCs remain and proliferate in the cultures. During the culturing period, the adherent fibroblasts and non-muscle cells are essentially depleted from successive cell cultures by passaging the cell suspension of muscle cells into new tissue culture dishes or flasks, which may or may not be collagen-coated. In the successive platings, adherent fibroblasts are removed. The muscle cells are successively passaged into new tissue culture dishes or flasks with new culture medium, e.g., at about 24 hour intervals, until MDCs remain enriched in the cultures as viable and proliferating cells, with virtually no fibroblastic cell component, for example, at the end of a series of more than about 2 platings, e.g., about 3-7 platings, 4-6 platings, or 3-5 platings. The end population of MDCs is enriched in cells that can form muscle fibers, e.g., myoblast cells or early muscle-derived cells, when injected into animal tissue, e.g., muscle tissue, in which the MDCs survive, repopulate and proliferate. This resulting end MDC population is introduced into a host in need of treatment, e.g., for the treatment of neurodegenerative disease. If desired, such MDCs can also be transfected or transduced with vectors, which can express gene products, e.g., heterologous gene products, such as growth factors, growth factor receptors, peptide neurotransmitters, or enzymes involved in the synthesis of neurotransmitters, including those for amino acids, biogenic amines, and neuropeptides.

In a particular aspect, the present invention involves a method of supporting the innervation of transplanted or grafted tissue, or the regeneration of nerve tissue employing MDCs, which, when introduced into a tissue environment, proliferate and survive for days, weeks, months or longer, to support innervation or regeneration of nerve tissue. When injected into a site of tissue in need of repair of nerve cells and tissue, MDCs can be exposed to factors, signals, and other components of the environmental milieu in which they are introduced or transplanted. Alternatively, the MDCs can be engineered to contain and express certain proteins that improve or promote and/or enhance innervation of transplanted or grafted tissue, or repair of muscle and/or nerve cell growth. Accordingly, in a nerve tissue environment, the cues produced or transmitted can influence the development of cells of the neuronal lineage to repair a defect, injury, damage, and the like in that environment.

The present invention also provides a cell based therapeutic method for treating, repairing, or assisting in the recovery of diseased, injured, damaged, or dysfunctional muscle tissue, and accompanying nerve cell or tissue damage, utilizing MDCs isolated and enriched from skeletal muscle as described herein. In this aspect, this invention provides MDCs as a cell based therapy for the treatment of nerve tissue damage contributing to various genitourinary dysfunctions, particularly following radical pelvic surgeries, such as prostatectomy, particularly, post-radical prostatectomy, in which the nerve tissue, e.g., cavernous nerve tissue and/or pelvic nerve tissue, becomes damaged. Also in this aspect, this invention provides MDCs as a cell based therapy for the treatment of erectile dysfunction, which frequently accompanies prostatectomy, particularly, post-radical prostatectomy in which cavernous nerve tissue and/or pelvic nerve tissue become damaged. In accordance with the present invention, MDCs promote neuronal survival and regeneration and can also can support the innervation of tissue that is, for example, damaged, injured, diseased, or transplanted, thus allowing repair of the nerve tissue, along with providing treatment and improvement of the associated dysfunction, such as erectile dysfunction, following surgery. This aspect of the invention is also useful in pelvic nerve repair; damage to pelvic nerves can occur during prostatectomy and other pelvic surgeries. Injury to these nerves is associated with bladder voiding disorders, such as described in Example 5 herein. Accordingly, MDCs of this invention are advantageous in the treatment of intrinsic sphincter deficiency caused by denervation of the urethral sphincter muscle. MDCs according to this aspect can be administered either at the site of nerve injury or at the site of innervation in the target organ, e.g., the penis, bladder or sphincter, or at both sites.

A further aspect of the present invention provides a method of treating or repairing both nerve and muscle tissue damage, injury, or dysfunction at the same time, preferably at the same site or in the same location, such as is exemplified by the repair of nerve tissue damage that is associated with erectile dysfunction and pelvic nerve damage. In a particular aspect, MDCs promote or enhance neurorecovery and the recovery of erectile function, or bladder function, following prostate surgery. In another aspect, MDCs promote or enhance neurorecovery and the recovery of pelvic nerve function following prostatectomy or pelvic surgery. The method involves introducing MDCs at a site of damage, injury, or dysfunction involving both nerve and muscle tissue, and allowing the cells to proliferate, differentiate and repopulate the area so as to repair the nerve and muscle tissues in a patient in need thereof.

Additional aspects, features and advantages afforded by the present invention will be apparent from the detailed description and exemplification hereinbelow.

DETAILED DESCRIPTION OF THE INVENTION

The present invention involves cell-based therapy methods for treating, repairing, ameliorating, or alleviating neurodegenerative diseases and injury, disease, damage, or dysfunction of nerve and/or muscle tissues and organs using muscle-derived cells (MDCs), e.g., myoblasts, or early muscle-derived cells, isolated from muscle tissue starting material, such as a skeletal muscle cell population. A method for obtaining MDCs for such treatments is described herein; methods have also been described in U.S. Pat. No. 6,866,842 and U.S. Pat. No. 7,115,417, the contents of which are herein incorporated by reference in their entireties.

The present invention provides accessible sources of somatic early muscle cells, particularly autologous cells, which are useful in the treatment and repair of neurodegenerative damage, and of diseases, disorders and injuries to nerve cells and tissue, such as, for example, in neuromuscular diseases. If applicable, e.g., for diseases, disorders, injuries, or dysfunctions involving both nerve and muscle tissues, particularly in the same vicinity, the MDCs also advantageously serve to treat and repair muscle-related injury, disease, damage, or dysfunction.

In addition and if desired or needed, the MDCs can be genetically modified to contain an expression vector, e.g., plasmid or viral, containing one or more heterologous polynucleotides which are expressed and whose expression products are produced at the site at which the MDCs are introduced in vivo. Accordingly, the cells may be genetically engineered to contain one or more nucleic acid sequence(s) encoding one or more active biomolecules, and to express these biomolecules, including proteins, polypeptides, peptides, hormones, metabolites, drugs, enzymes, and the like. Thus, the MDCs can serve to express biologically active substances, e.g., a neurotransmitter or growth factor, and may act as a long-term local delivery system for such substances at or near a site of injury, damage, disease, or dysfunction.

The MDCs can be genetically engineered by a variety of molecular techniques and methods known to those having skill in the art, for example, transfection, infection, transduction, or direct DNA injection. Transduction as used herein commonly refers to cells that have been genetically engineered to contain one or more foreign or heterologous product-encoding polynucleotides via the introduction of a viral or non-viral vector into the cells. Viral vectors are preferred. Transfection more commonly refers to cells that have been genetically engineered to contain one or more foreign product-encoding polynucleotides harbored in a plasmid, or non-viral vector. MDCs can be transfected or transduced by different vectors and thus can serve as gene delivery vehicles to allow gene products of interest to be expressed and produced at and around the tissue or organ site.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by precipitation with DEAE-Dextran or calcium phosphate (Graham and Van Der Eb, 1973, *Virology*, 52:456-467; Chen and Okayama, 1987, *Mol. Cell. Biol.* 7:2745-2752; Rippe et al., 1990, *Mol. Cell. Biol.*, 10:689-695); gene bombardment using high velocity microprojectiles (Yang et al., 1990, *Proc. Natl. Acad. Sci. USA*, 87:9568-9572); microinjection (Harland and Weintraub, 1985, *J. Cell Biol.*, 101:1094-1099); electroporation (Tur-Kaspa et al., 1986, *Mol. Cell. Biol.*, 6:716-718; Potter et al., 1984, *Proc. Natl. Acad. Sci. USA*, 81:7161-7165); DNA (vector)-loaded liposomes (Fraley et al., 1979, *Proc. Natl. Acad. Sci. USA*, 76:3348-3352); lipofectamine-DNA complexes; cell sonication (Fechheimer et al., 1987, *Proc. Natl. Acad. Sci. USA*, 84:8463-8467); receptor-mediated transfection (Wu and Wu, 1987, *J. Biol. Chem.*, 262:4429-4432; Wu and Wu, 1988, *Biochemistry*, 27:887-892); and the like. In one alternative, the retroviral or plasmid vector can be encapsulated into a liposome, or coupled to a lipid, and then introduced into a cell. In addition, cDNA, synthetically produced DNA, or chromosomal DNA can be employed as vector inserts utilizing methods and protocols known and practiced by those having skill in the art.

Standard protocols for producing replication-deficient retroviruses, including the steps of 1) incorporating exogenous genetic material into a plasmid; 2) transfecting a packaging cell line with plasmid and production of recombinant retroviruses by the packaging cell line; 3) collecting viral particles from tissue culture media; and 4) infecting the target cells with viral particles, are provided in, e.g., M. Kriegler, 1990, "Gene Transfer and Expression, A Laboratory Manual," W.H. Freeman Co., NY; and E. J. Murry, Ed., 1991, "Methods in Molecular Biology," vol. 7, Humana Press, Inc., Clifton, N.J.

Expression vectors containing all the necessary elements for expression are commercially available and known to those skilled in the art. See, e.g., Sambrook et al., 1989, *Molecular Cloning: A Laboratory Manual*, Second Edition, Cold Spring Harbor Laboratory Press, Cold Spring Harbor, N.Y.; F. M. Ausubel et al. (eds), 1995, *Current Protocols in Molecular Biology*, John Wiley & Sons, Inc., New York, N.Y.; D. N. Glover (ed), 1985, *DNA Cloning: A Practical Approach, Volumes I and II*; M. L. Gait (ed), 1984, *Oligonucleotide Synthesis*; Hames and Higgins (eds), 1985, *Nucleic Acid Hybridization*; Hames and Higgins (eds), 1984, *Transcription and Translation*; R. I. Freshney (ed), 1986, *Animal Cell Culture; Immobilized Cells and Enzymes*, 1986, (IRL Press); Perbal, 1984, *A Practical Guide to Molecular Cloning, The Series*, Methods in Enzymology, Academic Press, Inc.; J. H. Miller and M. P. Calos (eds), 1987, *Gene Transfer Vectors for Mammalian Cells*, Cold Spring Harbor Laboratory; Wu and Grossman (eds), *Methods in Enzymology*, Vol. 154; Wu (ed), *Methods in Enzymology*, Vol. 155.

Illustrative examples of vehicles or vector constructs for transfection or infection of MDCs according to an embodiment of the present invention include replication-defective viral vectors, DNA virus or RNA virus (retrovirus) vectors, such as adenovirus, herpes simplex virus, modified HIV vectors, and adeno-associated viral vectors. Preferred are adenovirus vectors. Such vectors include one or more promoters for expressing a heterologous molecule, e.g., a bioactive molecule (e.g., protein, polypeptide, or peptide). Suitable promoters which can be employed include, but are not limited to, adenoviral promoters, such as the adenoviral major late promoter; heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAl promoter; human globin promoters; viral thymidine kinase promoters, such as the Herpes Simplex Virus thymidine kinase promoter; retroviral LTRs (including modified retroviral LTRs); the β-actin promoter; and human growth hormone promoters. The promoter also may be the native promoter that controls the nucleic acid sequence encoding the polypeptide. Preferred viral vectors are typically derived from non-cytopathic eukaryotic viruses in which non-essential genes have been replaced with the nucleic acid sequence(s) of interest. Non-cytopathic viruses include retroviruses, which replicate by reverse transcription of genomic viral RNA into DNA with subsequent proviral integration into host cellular DNA.

Retroviruses have been approved for human gene therapy trials. In general, the retroviruses are replication-deficient, i.e., capable of directing synthesis of the desired proteins, but incapable of manufacturing an infectious particle. Retroviruses from which the retroviral plasmid vectors can be derived include, but are not limited to, Moloney murine leukemia virus, spleen necrosis virus, retroviruses such as Rous sarcoma virus, Harvey sarcoma virus, avian leukosis virus, gibbon ape leukemia virus, human immunodeficiency virus, adenovirus, myeloproliferative sarcoma virus, and mammary tumor virus. In general, the retroviruses used to create a viral vector are preferably debilitated or mutated in some respect to prevent disease transmission. If desired, infectious replication-defective viral vectors may be used to genetically engineer the cells prior to in vivo injection of the cells. In this regard, the vectors may be introduced into retroviral producer cells for amphotrophic packaging. The natural expansion of muscle-derived progenitor cells into adjacent regions obviates a large number of injections into or at the site(s) of interest.

The vectors are typically substantially free of any prokaryotic DNA and may comprise a number of different functional nucleic acid sequences. Examples of such functional sequences include nucleic acid, e.g., DNA or RNA, sequences comprising transcriptional and translational initiation and termination regulatory sequences, including promoters (e.g., strong promoters, inducible promoters, and the like) and enhancers, which are active, for example, in esophagus or small intestine cells. Also included as part of the functional sequences is an open reading frame (nucleic acid sequence) encoding a protein, polypeptide, or peptide of interest. Flanking sequences may also be included for site-directed integration. In some situations, the 5'-flanking sequence allows for homologous recombination, thus changing the nature of the transcriptional initiation region, so as to provide for inducible or noninducible transcription to increase or decrease the level of transcription, as an example.

The vector employed generally also includes an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the MDCs themselves. Such replication systems are represented by replication-defective adenoviruses constructed as described, for example, by G. Acsadi et al., 1994, *Hum. Mol. Genet* 3:579-584, and by Epstein-Barr virus. Examples of replication defective vectors, particularly retroviral vectors that are replication defective, are BAG, described by Price et al., 1987, *Proc. Natl. Acad. Sci. USA*, 84:156; and Sanes et al., 1986, *EMBO J.*, 5:3133. It will be understood that the final gene construct can contain one or more genes of interest, for example, a gene encoding a bioactive metabolic molecule.

In general, the nucleic acid sequence desired to be expressed by the MDCs is that of a structural gene, or a functional fragment, segment or portion of the gene, which is heterologous to the cell serving as delivery vehicle and which encodes a desired protein or polypeptide product. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, suppressor molecules, cell differentiation factors, cell signaling factors and programmed cell death factors.

Preferably, a marker is present for the selection of cells containing the vector construct. The marker may be an inducible or non-inducible gene and will generally allow for positive selection under induction, or without induction, respectively. Examples of commonly used marker genes include neomycin, dihydrofolate reductase, glutamine synthetase, and the like. The vector employed also generally includes an origin of replication and other genes that are necessary for replication in the host cells, as routinely employed by those having skill in the art. As an example, the replication system comprising the origin of replication and any proteins associated with replication encoded by a particular virus may be included as part of the construct.

In one embodiment, the final gene construct preferably contains at least one gene or polynucleotide sequence encoding a product, preferably a biologically active product, which is useful in the treatment of a given disorder of the central or peripheral nervous system. In some instances, the biologically active product is useful in treating a muscle-related disorder, disease, or dysfunction. In other aspects, such as treatment of both nerve and muscle disorders, diseases, or dysfunctions at one time, one or more genes or polynucleotides encoding a product for affecting nerve cells/tissue, and one or more genes or polynucleotides encoding a product for affecting muscle cells/tissue are provided. A growth factor product may be expressed and secreted; such a product includes proteins, peptides, mitogens, or other molecules having an effect on growth, proliferation, differentiation, or tropism. Nonlimiting examples of growth factor products that are able to be employed to treat CNS disorders include nerve growth factor (NGF), ciliary neurotrophic factor (CNTF), brain-derived neurotrophic factor (BDNF), neurotrophin 3, neurotrophin 4, interleukins, fibroblast growth factors 1 and 2 (FGF-1, FGF-2), insulin-like growth factors, glucocorticoid hormone, somatostatin, platelet-derived growth factor (PDGF), tetanus toxoid, TGF-alpha and beta, epidermal growth factor and retinoic acid. In addition, the MDCs can be modified to express and produce a growth factor receptor, such as receptors for the aforementioned growth factors, or the trk family of neurotrophin receptors (e.g., trk, trkB, trkC), or to express and produce a neurotransmitter, or receptors thereof, for example, serotonin, L-dopa, dopamine, tachykinin, substance P, epinepherine and norepinepherine, enkephalin, GABA, acetylcholine, glutamate, glutamine, histamine, and the like.

For MDC-based treatments, a skeletal muscle explant is preferably obtained from an autologous or heterologous (e.g., allogeneic) human or animal source. An autologous animal or human source is particularly suitable. However, allogeneic, or non-autologous donors, including human adult, fetal, embryonic, or placental donor cell sources of MDCs, as well as xenogeneic sources, are embraced by this invention. In the case of the CNS, the use of donor MDCs that are xenogeneic to the host may not be as critical as for other sites of the body, as the CNS itself tends to be immunoprivileged. Thus, the immune response to xenografts, when there is one, is significantly reduced, relative to reactions elsewhere in the body. However, to ensure that xenografts, when utilized, are not rejected, a method of reducing or eliminating the immune response to the introduced or implanted cells or tissue can be employed. Accordingly, hosts or recipients can be immunosuppressed, either through the use of immunosuppressive drugs (e.g., cyclosporin), or through local immunosuppression treatments using locally applied immunosuppressants (e.g., U.S. Pat. No. 5,026,365 to Rossini describes encapsulation methods for local immunosuppression). Alternative methods can involve gene replacement or knockout using homologous recombination, such as to ablate genes for MHC or HLA to reduce antigenicity of donor cells; surface modification; or tissue typing to match histocompatibility types of the donor and recipient, particularly for allogeneic donor cells. (See also, for example, U.S. Pat. No. 6,497,872 to Weiss et al.).

To introduce or transplant the MDCs and/or compositions comprising the MDCs according to the present invention into a recipient host, preferably mammalian, including humans, a suspension of mononucleated MDCs is prepared, preferably from a skeletal muscle source or an autologous skeletal muscle source as described herein. MDCs are introduced or administered into tissues or organs in a recipient (an animal, e.g., mammals, including humans), in an amount effective to repopulate and regenerate in the tissue or organ. The effective amount of MDCs for the treatment, repair, promotion, enhancement, or amelioration of an injury, condition, pathology, disorder, or damage to a tissue or organ can be determined by standard clinical techniques. An "effective amount" or a "pharmaceutically effective amount" of the MDCs refers to an amount effective for treating, repairing, promoting, enhancing, ameliorating, and the like, a disease, condition, pathology, disorder, injury, damage, or dysfunction for which the MDCs are being used according to this invention. In a particular embodiment, an effective amount of MDCs comprises the amount effective for promoting or enhancing axonal regeneration and/or neuronal survival at the site of nerve damage, disease or injury; in another embodiment, an effective amount of MDCs comprises the amount effective for promoting or enhancing innervation in tissue associated with nerve damage or neuropathy; in another embodiment, an effective amount of MDCs comprises the amount effective for repairing peripheral nerve and muscle tissue at the same tissue site or location; in another embodiment, an effective amount of MDCs comprises the amount effective for promoting or enhancing innervation of tissue or organ transplants or grafts in a host tissue or organ; in another embodiment, an effective amount of MDCs comprises the amount effective in supporting the regeneration of peripheral nerves, in particular autonomic nerves, injured during radical pelvic surgery, in particular radical prostatectomy; in another embodiment an effective amount of MDCs comprises the amount effective for promoting or enhancing innervation of tissue following prostatectomy; and in another embodiment, an effective amount of MDCs comprises the amount effective for promoting or enhancing innervation of a severed or partially severed tissue or limb subject to surgical re-attachment; in another embodiment, an effective amount of MDCs comprises the amount effective for preventing or retarding degeneration of peripheral cutaneous exons following damage or injury. Such effective amounts can be the same or different for the encompassed embodiments and are readily determined by the practitioner. If another therapeutic agent is used in conjunction with the MDCs in a formulation for administration, the effective amount of the therapeutic agent refers to an amount effective for providing the therapeutic effect of the therapeutic agent. The precise dose to be employed in the formulation will also depend on the route of administration, as well as an individual patient's circumstances, such as age, health and vital statistics, and the severity of the disease, condition, or disorder. Dosing should be decided according to the judgment of the medical practitioner based on an evaluation of the patient and considerations of a patient's physiologic situation and medical history. In addition, in vitro assays may optionally be used to assist in determining optimal dosage ranges. Effective doses can be extrapolated from dose-response curves derived from in vitro or in vivo animal model test systems.

The MDCs can comprise compositions, including suspensions. Such suspensions contain the MDCs of the invention in a physiologically-acceptable carrier, excipient, or diluent. The number of cells in an MDC suspension and the mode of administration may vary depending on the site and condition being treated. As a non-limiting example in accordance with the present invention, about $1\text{-}1.5\times10^4$ to $1.5\times10^{10}$, or about $1\text{-}1.5\times10^6$ to $1\text{-}1.5\times10^8$, or about $1\text{-}1.5\times10^6$ MDCs are injected for the treatment of an approximately 8 mm diameter region of tissue or organ damage, e.g., to an area comprising muscle and/or nerve tissue. It is to be understood that a skilled practitioner can determine and modulate the amounts of MDCs for use in MDC-based treatments according to requirements, limitations, and/or optimizations determined for each case. Additional non-limiting examples of compositions comprising MDCs include tissue-engineered constructs, e.g., collagen-containing scaffolds and matrices, small intestinal submucosa (SIS), and SIS gel, for example, as disclosed in co-pending U.S. patent application Ser. No. 10/081,835, the contents of which are hereby incorporated herein by reference. Such constructs are particularly advantageous in providing a support structure for the MDCs and in preventing undesirable migration of MDCs from the site of injection or implantation.

Suspensions of MDCs for administering to a subject can comprise, for example, about $10^4$ to $10^{10}$ cells/ml, or about $10^4$ to $10^8$ cells/ml, or about $10^4$ to $10^6$ cells/ml in a sterile solution, e.g., physiological saline or complete medium modified to contain the subject's serum, as an alternative to fetal bovine serum. Alternatively, MDC suspensions can be in serum-free, sterile solutions, such as cryopreservation solutions (Celox Laboratories, St. Paul, Minn.). The MDC suspensions can then be introduced e.g., via injection, into one or more sites of the donor tissue or organ. The introduction of MDCs, e.g., by injection or transplantation, to areas of the central and peripheral nervous systems that have been damaged, allows repair of such injury or damage, such as by the production of appropriate cell types, by the repair of injured or damaged circuitries, by promoting or enhancing nerve cell innervation and/or by the provision of neurotransmitters to restore or ameliorate neurological function. MDCs provide a reliable source of cells that are neither tumorigenic nor immortalized by transfection or transformation.

Animal models of neurological disorders and CNS or peripheral nerve damage are suitable for the demonstration of the effectiveness of the MDCs used in treating neurological disorders, damage and injury. For example, the MDCs can be administered to any animal with abnormal neurological or neurodegenerative symptoms obtained in any manner, including being obtained as a result of mechanical, chemical, or electrolytic lesions, of experimental manipulations, such as aspiration of neural areas, cryodamage to neural tissue or cells, or of aging processes. Mice and rats are illustrative of acceptable model systems.

MDCs can be administered as a pharmaceutically or physiologically acceptable preparation or composition containing a physiologically acceptable carrier, excipient, or diluent, and administered to the tissues of the recipient animal of interest, including humans and non-human mammals. The MDC-containing composition can be prepared by resuspending the cells in a suitable liquid or solution such as sterile physiological saline or other physiologically acceptable injectable aqueous liquids. The amounts of the components to be used in such compositions can be routinely determined by those having skill in the art. Growth factors and the like may also be administered, or co-administered before, after, or with the administration of MDCs.

The MDCs, or compositions thereof, can be administered by parenteral routes of injection, including subcutaneous, intravenous, intramuscular, and intrasternal. Other modes of administration include, but are not limited to, intranasal, intrathecal, intracutaneous, percutaneous, enteral, injection cannula, timed release, oral and sublingual routes. In one embodiment of the present invention, administration of the MDCs can be mediated by endoscopic surgery. For the treatment of various neurological diseases or disorders that affect the brain, MDCs can be introduced into the tissues lining the ventricles of the brain. The ventricular system of nearly all brain regions permits easier access to different areas of the brain that are affected by the disease or disorder. For example, for treatment, a device, such as a cannula and osmotic pump, can be implanted so as to administer MDCs, genetically modified MDCs, or MDCs and growth factors, preferably comprising a pharmaceutically acceptable composition. Direct injection of the MDCs into tissues, e.g., ventricular tissue, is also a suitable mode of administration. Thereafter, the MDCs can migrate into those regions that are in need of treatment as a result of disease or injury. For example, the close proximity of the ventricles to many brain regions is conducive to the diffusion of a secreted or introduced neurological substance in and around the site of treatment by the MDCs or their progeny.

For administration to a recipient, for example, injectable administration, the composition comprising MDCs is in sterile solution or suspension or can be resuspended in pharmaceutically- and physiologically-acceptable aqueous or oleaginous vehicles, e.g., SIS gel, which may contain preservatives, stabilizers, and material for rendering the solution or suspension isotonic with body fluids (i.e. blood) of the recipient. Non-limiting examples of excipients suitable for use include water, phosphate buffered saline (pH 7.4), 0.15M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

To optimize the success of cell-based treatment, for example, in tissue or organ transplants and grafts, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the injection or transplant procedure. For example, cyclosporin A or other immunosuppressive drugs can be administered to the transplant recipient. Immunological tolerance may also be induced prior to transplantation by alternative methods known in the art (e.g., D. J. Watt et al., 1984, *Clin. Exp. Immunol.* 55:419; D. Faustman et al., 1991, *Science* 252: 1701).

Consistent with the present invention, the MDCs can be administered to CNS and peripheral nervous system tissues, comprising nerve cells or other cell types, such as the brain, spinal cord, periphery, as well as to muscle tissue (i.e., skeletal/striated or smooth muscle), to treat various diseases, dysfunctions, injuries and damage in an animal having abnormal neurological or neurodegenerative symptoms, disorders, conditions, or effects. Demyelinating diseases, peripheral nerve degeneration and muscular dystrophic disease are examples of conditions for which the cells and methods of the present invention are suitable. For those neurological diseases and disorders in which areas of the forebrain are affected, e.g., Parkinson's disease, Huntington's disease, or Alzheimer's disease, MDCs, MDCs expressing neurological or growth factors, and/or MDCs and growth factors can be introduced into the ventricles of the forebrain. As a more specific example, for Parkinson's disease, the striatum is affected by low levels of dopamine. Thus, MDCs and dopamine, e.g., MDCs expressing dopamine, or MDCs administered in conjunction with dopamine, can be used (for example, administered to the lateral ventricle) to treat or repair the affected cells of the striatum and provide dopamine to increase the levels of this neurologic compound where needed. Such a use provides advantages over the use of the drug L-dopa to which patients can develop tolerance or adverse side effects over time. For CNS tissue immediately surrounding a ventricle, treatment can comprise administration to the lumbar cistern for circulation throughout the CNS. For treating motor neuron diseases, such as Amyelotrophic Lateral Sclerosis (ALS), or for treating demyelinating diseases, such as MS, MDCs alone, or MDCs in combination with other treatment substances, can be administered to the central canal.

The MDCs and methods employing MDCs can be used to treat a variety of CNS and peripheral nervous system disorders, diseases and injuries. Non-limiting examples of neurodegenerative disorders, diseases and injuries serving as targets for treatment include, for example, Parkinson's disease and its associated dyskinesias; Alzheimer's disease; multiple sclerosis (MS); amyolotrophic lateral sclerosis (ALS); Huntington's disease; acute brain injury, for example, stroke, cerebral palsy, head injury; spinal cord trauma, injury, or infection; diabetes; and other CNS dysfunctions, for example, epilepsy, depression, schizophrenia, and palsies; and peripheral nerve injury, degeneration or inflammation. Other diseases encompass demyelinating diseases, such as cerebral sclerosis, diffuse cerebral sclerosis, disseminated pervenous encephalomyelitis, neuromyelitis optica, multiple sclerosis (Charcot and Marburg types), neuromyelitis optica, concentric sclerosis, acute disseminated encephalomyelitis, post encephalomyelitis, postvaccinal encephalomyelitis, acute ahemorrhagic leukoencephalopathy, progressive multifocal leukoencephalopathy, idiopathic polyneuritis, diphtheric neuropathy, Pelizaeus-Merzbacher disease, central pontine myelinosis, spongiform leukodystrophy and leukodystrophy (Alexander type).

In other embodiments, MDCs and methods employing MDCs can be used to promote and/or enhance the survival and/or growth of neuronal processes, e.g. axons and dendrites, between transplanted tissues or organs and host tissues or organs. A nonlimiting example includes the grafting of autologous, allogeneic, or xenogeneic skin or skin substitute, for example, in the repair of severe burn injury or other dermal tissue insult where damage to peripheral nerves has occurred. Yet another nonlimiting example includes the use of MDCs in accordance with the present invention to promote and/or enhance neuronal survival and innervation or re-innervation of severed limbs or organs subject to surgical re-attachment. In a related example, MDCs can be used to promote and/or enhance the innervation of transplanted autologous, allogeneic, or xenogeneic tissues and organs.

Another embodiment embraced by the present invention involves the use of MDCs in the treatment of neurogenic back pain and other painful conditions associated with damage or disease of the lumbar spine, e.g., sciatica. Back pain, particularly lower back pain, frequently results from injury to, or irritation of, the spinal nerves due to lumbar radiculopathy, bony encroachment, or viral inflammation. MDCs in accordance with the present invention can provide support for the recovery of damaged or injured nerves associated with diseases, conditions, or disorders of the back, spine, or vertebrae, thus reducing pain.

MDCs are particularly advantageous in the treatment of demyelinating diseases. MDCs introduced at a site requiring remyelination can serve as a beneficial remyelination therapeutic. The MDCs can be injected one or more times into a site near or around the demyelinated target area, i.e., one having demyelinated axons, in order to introduce the MDCs so that they can associate with demyelinated axons for repair. In addition, the MDCs, as observed by β-galactosidase marker expression, have been shown to survive for long periods of time, e.g., greater than 4 weeks, and up to 10 weeks, or longer following introduction into the brain, thereby substantiating their usefulness and effectiveness as treatment and therapy for neurodegenerative diseases, disorders and injury.

In another embodiment, cultures of MDCs, or clones or subclones thereof, or MDCs that have been exposed to a neurotrophic or neurological factor such as NGF, can be used in the screening of potentially therapeutic drugs, compounds, agents, substances, or compositions. These test substances, in varying amounts and for various times, can be added to MDCs in culture to determine or monitor the response of the cells to the test substance. Modulation in cell growth and alterations in physical characteristics of the cells can be determined by observing cell proliferation using a microscope, with or without other known techniques, such as immunostaining and the like. Should the expression of new or increased levels of proteins such as enzymes, receptors, other cell surface molecules, or of neurotransmitters, amino acids, neuropeptides, or biologic amines be induced by a test substance, techniques known and practiced in the art can be used to identify the levels, or changes thereof, of such molecules. Such techniques include, illustratively without limitation, immunohistochemistry using antibodies directed against specific molecules, or biochemical analyses, such as protein assays, enzyme assays, receptor binding assays, enzyme linked immunosorbant assays (ELISAs), Radioimmunoassays (RIAs), Western blots, and high performance liquid chromatography (HPLC). For nucleic acid analysis, Northern blots can be used to determine mRNA levels for the molecules, or for enzymes that produce the molecules; polymerase chain reaction (PCR) can also be used.

In a related embodiment, cultures of MDCs, or clones or subclones thereof, prepared as described herein can be used to screen test substances, compounds, drugs, pharmaceuticals, chemicals, and other agents for their potential to act as neurologic drugs, which may improve or augment the ability of MDCs to promote or enhance nerve treatment and repair. These test materials, in varying amounts and for various times, can be added to MDCs in culture. The MDCs can then be examined using routine assays, such as immunostaining, to determine if the exposed cells are induced to differentiate into a neuronal phenotype in response to the test material.

As conventionally known in the art, commercially available reagents, such as antibodies, can be used to determine cell markers and identifying surface proteins, which are typically expressed on the cell surface. For example, for nerve cell types, the O4 antibody (Boerhinger Mannheim) binds to oligodendrocytes and their precursors; several available antibodies bind to astrocytes, e.g., the RAN2 antibody (ATCC TIB-119; as well as ATCC CRL-2534, CRL-2535, or CRL-2541; and antibodies to tetanus toxoid (TT, Boerhinger Mannheim) bind to neurons. Other antibodies directed to markers such as desmin, CD56, Sca-1, etc. are available for determining cell surface marker profiles of cells. Using cultures of MDCs, screening and testing methods can be carried out to assess potential harmful affects of biological agents (e.g., drugs) on proliferation, or on the survival or function of these cells used in the described methods. As a guide, cells can be plated at a density of about $5-10 \times 10^5$ cells/ml, or about $5-10 \times 10^6$ cells/ml.

The effects of biological agents on cells such as neuronal cells, or MDCs, are determined based on significant differences relative to one or more control cultures with respect to phenotypic changes, ratios of expressed phenotypes, cell viability and gene expression changes. Nonlimiting examples of biological agents include trophic factors that are added to the culture medium, such as EGF, FGF, BDNF, CNTF, TGFα, GDNF and the like. FGF is known to increase the ratio of neurons; CNTF is known to increase the ratio of oligodendrocytes. Physical alterations to the cells can be analyzed by observing cell morphology and growth via microscopy. Electro-physiological analyses can be employed to determine whether any of the test biological agents affect cell membrane characteristics, such as resting membrane potential, evoked potentials, the direction and ionic character of current flow, and the dynamics of ion channels. These types of analyses can be performed using any method practiced in the art for making the analyses, for example, extracellular single unit voltage recording, intracellular voltage recording, voltage clamping, patch clamping and calcium imaging techniques. These methods can also include the use of voltage sensitive dyes, optical imaging and ion sensitive electrodes. Such treated cells, preferably comprising a physiologically acceptable composition, can be transplanted into animals for further in vivo evaluation, such as for determining long-term survival, as well as for various immunological and biochemical characteristics, and in treating or supporting the treatment of neurological diseases and disorders.

In another embodiment, the present invention provides ex vivo gene delivery to cells and tissues of a recipient mammalian host, including humans, through the use of MDCs that are introduced into a tissue site of a recipient host animal. The MDCs can also be virally transduced using an adenoviral vector engineered to contain a heterologous gene encoding a desired gene product. Such an ex vivo approach provides the advantage of efficient viral gene transfer, which can be more efficient than direct gene transfer approaches. The ex vivo procedure involves the use of MDCs obtained and isolated from muscle tissue. The muscle biopsy that serves as the source of MDCs can be obtained from an injury site or from another area that may be more easily obtainable from the clinical surgeon.

It will be appreciated that in accordance with the present invention, clonal isolates can be derived from the population of MDCs using various procedures known in the art, for example, limiting dilution plating in tissue culture medium. Clonal isolates comprise genetically identical cells that originate from a single, solitary cell. In addition, clonal isolates can be derived using FACS analysis, followed by limiting dilution, to achieve a single cell per well to establish a clonally isolated cell line. MDC clonal isolates can be utilized in the present methods, as well as for engineering the cells for the expression of one or more bioactive molecules, or in gene therapies.

In another embodiment, MDCs are first infected with engineered viral vectors containing at least one heterologous polynucleotide encoding a desired product, suspended in a physiologically acceptable carrier or excipient, such as saline or phosphate buffered saline, and then administered to an appropriate site in the host. Consistent with the present invention, the desired product is expressed by the injected cells, which thus introduced the product into the host. The introduced and expressed products can be utilized to treat, repair, or ameliorate the injury, dysfunction, or disease, due to expression over long time periods by the MDCs of the invention, having long-term survival (greater than 2 weeks, preferably greater than 4 weeks, more preferably greater than 6 weeks, and most preferably, greater than 8 weeks) in the host tissue.

Illustratively, and without limitation, approximately $10^5$ to $10^{12}$, or $10^6$ to $10^{12}$, or $10^6$ to $10^8$, or $10^8$ to $10^{12}$, or $10^8$ to $10^{10}$, or $10^{10}$ to $10^{12}$ MDCs suspended in a physiologically compatible medium can be implanted into desired tissue for gene therapy for a 70 kg human. This number of MDC of the invention can be produced from a single 100 mg skeletal muscle biopsy from a human source. For the treatment of a specific injury site, an injection of genetically engineered MDCs into a given tissue or site of injury comprises a therapeutically effective amount of cells in solution or suspension, e.g., about $10^5$ to $10^6$ cells per cm$^3$ of tissue to be treated, in a physiologically acceptable medium.

In another embodiment of the invention, human fetal or embryonic MDCs can be employed in transplant methodologies and treatments, under appropriate guidelines and approved conditions and regulations, with minimal to no problems of rejection due to potential donor-host incompatibilities. For example, human MDCs from fetal limb muscle (early skeletal muscle) were found to be immunotolerant and to exhibit high levels of survivability, as they were able to persist in SCID mice for >2 weeks post injection. (See, for example, PCT/US01/12084). Thus, under the appropriate guidelines, regulations and conditions, human fetal MDCs may be used and enriched by successive platings for treatments and transplant or grafting as described herein.

Another embodiment of the present invention encompasses the use of MDCs to promote and/or enhance the innervation, or re-innervation, of transplanted or grafted tissues or organs. A specific yet non-limiting example involves the use of transplanted tissue in the treatment of burn injury. Burn-related injuries are frequently accompanied by damage to cutaneous peripheral nerves, resulting in hyperaesthesia, dysaesthesia and other sensory deficits. Currently, autologous full-thickness skin grafts, free flaps, and pedicle flaps are the treatment options that are capable of restoring sensory function. However, even under optimal conditions, sensation remains impaired due to incomplete innervation of the transplanted or grafted tissue. Moreover, in instances where a tissue-engineered skin substitute is used for transplant or grafting, e.g., a collagen matrix seeded with autologous keratinocytes and fibroblasts, the restoration of tactile sensation is even less satisfactory. The present invention allows for the application of MDCs to the site of a injury, such as a burn injury, to enhance the survival of injured peripheral neuronal processes, e.g., axons and dendrites, and to promote and/or enhance the innervation of transplanted or grafted tissues or organs, such as skin and skin substitutes. In an alternative embodiment according to the invention, MDCs can be injected or applied to the transplanted or grafted tissue or organ itself.

MDCs can also be seeded into any number of tissue-engineered constructs, or engineered materials, that serve as skin substitutes in order to promote and/or enhance nerve regeneration into the skin substitute. Such skin substitutes can comprise any of the following components, alone or in combination: acellular cadaveric skin matrix, poly-lactic acid, hyaluronic acid, poly-glycolic acid, polyethylene oxide, polybutylene terephthalate, silicone, autologous and/or allogeneic cultured fibroblasts, autologous and/or allogeneic cultured keratinocytes, autologous and/or allogeneic cultured epidermis, autologous and/or allogeneic cultured epithelium, de-epidermized dermis, collagen sponge, collagen-chitosan sponge, chitosan-cross-linked collagen-glycosaminoglycan matrix, collagen gel, polyglactin mesh, small intestinal submucosa (SIS). Also encompassed by this embodiment of the invention is the use of MDCs containing a heterologous nucleic acid sequence coding for the expression of various ameliorative proteins or polypeptides, including, but not limited to, nerve growth factor (NGF), neurotrophin 3 (NT3), brain-derived neurotrophic factor (BDNF), and glial cell derived neurotrophic factor (GDNF). It is to be understood that the above examples are intended to be representative and nonlimiting, as MDCs can also be administered to facilitate the innervation, or re-innervation, of other transplanted or grafted tissues, including, but not limited to, smooth muscle, skeletal muscle, vascular tissue and glandular tissue.

In an embodiment, the present invention embraces a method of promoting or enhancing innervation of tissue or organ transplants, or tissue or organ grafts in a host tissue or organ comprising: introducing muscle-derived cells (MDCs) into an area comprising a boundary between the tissue or organ transplant or graft and the host tissue or organ. As will be appreciated by the skilled practitioner, the MDCs can be injected or introduced at or near the border, margin, rim, edge or perimeter formed between a transplanted or grafted tissue or organ and the host's tissue or organ, or an area thereof. By virtue of this method, MDCs facilitate survival and growth of nerve fibers between the host tissue or organ and the tissue or organ transplant or graft, thus promoting innervation. In an embodiment of the method, the MDCs are autologous to either the host tissue or organ, or to the tissue or organ transplant or graft. In another embodiment of the method, the tissue or organ for transplanting or grafting is selected from digestive, reproductive, cardiovascular, urological, respiratory, epithelial, connective, neuronal, endocrine, skin, smooth muscle, skeletal muscle tissues or organs, or portions or sections thereof. In another embodiment of the method, the tissue or organ transplant or graft comprises a skin substitute or engineered material designed to have properties mimetic of natural tissue. In another embodiment of the method, the skin substitute or engineered material comprises one or more of acellular cadaveric skin matrix, poly-lactic acid, hyaluronic acid, poly-glycolic acid, polyethylene oxide, polybutylene terephthalate, silicone, autologous cultured fibroblasts, allogeneic cultured fibroblasts, autologous cultured keratinocytes, allogeneic cultured keratinocytes, autologous cultured epidermis, allogeneic cultured epidermis, autologous cultured epithelium, allogeneic cultured epithelium, de-epidermized dermis, collagen sponge, collagen-chitosan sponge, chitosan-cross-linked collagen-glycosaminoglycan matrix, collagen gel, polyglactin mesh, or small intestinal submucosa (SIS). In another embodiment of the method, the skin substitute or engineered material is introduced in combination with dermal tissue or dermal tissue components. Illustrative examples of dermal tissue or dermal tissue components include, without limitation, keratinocytes, fibroblasts, melanocytes, dendritic cells, adnexal cells, neuronal cells, glial cells, endothelial cells, or smooth muscle cells. In another embodiment of this method, the MDCs carry at least one heterologous polynucleotide encoding a heterologous protein or polypeptide for enhancing the innervation of transplanted tissues or organs. Examples of suitable proteins or polypeptides include, without limitation, one or more of a growth factor, a growth factor receptor, a peptide neurotransmitter, or an enzyme involved in the synthesis of neurotransmitters. More specifically, suitable growth factors include, without limitation, nerve growth factor (NGF), ciliary neurotrophic factor (CNTF), brain-derived neurotrophic factor (BDNF), neurotrophin 3, neurotrophin 4, interleukins, fibroblast growth factor 1 (FGF-1), fibroblast growth factor 1 (FGF-2), insulin-like growth factors (IGF), glucocorticoid hormone, somatostatin, platelet-derived growth factor (PDGF), tetanus toxoid, TGF-alpha, TGF-beta, epidermal growth factor, or retinoic acid. Suitable growth factor receptors include, without limitation, the trk family of neurotrophin receptors, nerve growth factor (NGF) receptor, ciliary neurotrophic factor (CNTF) receptor, brain-derived neurotrophic factor (BDNF) receptor, neurotrophin 3 receptor, neurotrophin 4 receptor, interleukin receptor, fibroblast growth factor 1 (FGF-1) receptor, fibroblast growth factor 1 (FGF-2) receptor, insulin-like growth factor (IGF) receptor, glucocorticoid hormone receptor, platelet-derived growth factor (PDGF) receptor, TGF-alpha receptor, TGF-beta receptor, epidermal growth factor (EGF) receptor, or retinoic acid receptor.

In another embodiment, the present invention embraces a method involving the use of MDCs as a cell based therapy for the treatment of erectile dysfunction, which frequently accompanies prostatectomy, particularly, post-radical prostatectomy, in which the nerve tissue, e.g., cavernous nerve tissue, becomes damaged. In accordance with the present invention, MDCs can support the innervation of tissue that is, for example, damaged, injured, diseased, or transplanted, thus allowing repair of the nerve tissue, along with providing treatment and improvement of erectile dysfunction. This feature is particularly advantageous in methods as described herein in Examples 2 and 4. In one embodiment, the invention encompasses a method of promoting or enhancing neurorecovery and recovery of erectile function following prostatectomy, comprising administering to a patient in need thereof autologous muscle-derived cells (MDCs) in an amount effective to promote or enhance neurorecovery and the recovery of erectile function in the patient. In an embodiment, the MDCs are administered at one or more sites of prostatectomy anastomosis. MDCs can also be administered in or around the cavernous nerves, pelvic nerves, hypogastric nerves, pelvic plexi, and pelvic autonomic ganglia, or into the penis. In an embodiment, MDCs are re-administered at a time following prostatectomy, for example, 6 months, 1 year or more, e.g., by cytoscopy. In another embodiment, the MDCs are enriched from a muscle cell suspension by plating the suspension into at least two successive cultures so as to eliminate fibroblasts and non-muscle cells and to enrich for an end population of mononucleated MDCs, which comprise myoblasts as the enriched muscle-derived cell population. In another embodiment, the MDCs are obtained from skeletal muscle tissue. In another embodiment, the MDCs are administered in an amount of about $10^5$ to $10^6$ cells per $cm^3$ of tissue of the patient. In another embodiment, the MDCs are administered in conjunction with a physiologically acceptable carrier, diluent, or excipient. In another embodiment, a cloned population of the MDCs is introduced into the patient.

In another embodiment, the invention embraces a method involving prevention or retardation of the degeneration of peripheral cutaneous axons that have been damaged, for example, by severe burn injuries, or insult, or blunt trauma to a tissue or organ, thereby enhancing the capacity of these axons to innervate autologous skin grafts.

EXAMPLES

The examples described below are provided to illustrate the present invention and are not included for the purpose of limiting the invention.

Example 1

Materials and Methods

Animals:
Normal mice (and Mdx mice (C57BL/10ScSn $DMD^{mdx}$/J), if used), were purchased from Jackson Laboratories; mdx/scid mice, if used, were obtained from the inbreeding of mdx and scid mice (C57BL/6J-$Prkdc^{scid}$/S2J, immunodeficient). The mdx mouse is characterized by a lack of dystrophin in the membrane of muscle fibers, which causes muscle fiber degeneration and necrosis. All animal protocols used for these experiments were approved by the Children's Hospital of Pittsburgh's IACUC committee (protocol nos. 7/00 and 3/02).

Muscle-Derived Cells (MDCs):
MDCs were obtained from primary skeletal muscle of C57BL/6J mice (5 days old) using a culturing technique involving successive or serial plating of the cells over two days or longer which yielded an enriched end population of mononucleated, desmin positive, myoblastic MDCs which, as a result of the muscle cell suspension being serially or successively passaged into new culture plates over at least two days, are essentially devoid of fibroblasts and non-muscle cells and are enriched for the viable end population of cultured MDCs. Clonal populations of cells obtained from this technique can be established by protocols as practiced in the art, e.g., limiting dilution.

MDC Isolation and Culture:
MDCs were isolated from a starting muscle tissue, e.g., skeletal muscle sample to obtain an enriched population of MDCs. To this end, a series of plating and culturing steps were carried out that resulted in enrichment of an end population of MDCs, which were characterized as early muscle-derived cells, such as myoblasts, that were viable, non-fibroblast, desmin-positive, mononucleated and formed myofibers. MDCs were isolated at the end of a serial plating, or a passaging/culturing protocol comprising successive platings of the muscle cell starting sample. During the successive platings of cells into new culture containers, MDCs (including myoblasts and early muscle-derived cells) were enriched and separated from non-MDC types, e.g., fibroblasts and adipocytes, endothelial cells, and connective tissue cells. The successive platings can be carried out for greater than about 2 days, e.g., about 3-7 days, or 4-6 days, or 3-5 days, until proliferating, non-fibroblast MDCs as described remained and dominated in the cultures. During the culturing period, the adherent fibroblasts and non-muscle cells were essentially depleted from successive cell cultures by passaging the cell suspension of muscle cells into new tissue culture dishes or flasks, which may or may not be collagen-coated. After the initial removal of adherent fibroblasts, which occurred from about 1 to 24 hours after placing the muscle cell starting sample in the culture containers, the cells were successively passaged into new tissue containers, i.e., new culture dishes or flasks, with new culture medium, e.g., at about 24 hour intervals, until an end population of MDCs remained enriched in the cultures as viable and proliferating cells, with virtually no fibroblastic cell component, for example, at the end of a series of about 2-7 platings, 3-7 platings, 4-6 platings, or 3-5 platings. This end population of MDCs was enriched in cells that formed muscle fibers, e.g., myoblast cells or early muscle-derived cells, and performed the functions as described herein when injected or introduced into animal tissues or organs, e.g., muscle tissue, in which the MDCs survived, repopulated and proliferated. If desired, such MDCs can also be transfected or infected with vectors, which can express gene products, e.g., heterologous gene products, such as growth factors, growth factor receptors, peptide neurotransmitters, or enzymes involved in the synthesis of neurotransmitters, including those for amino acids, biogenic amines, and neuropeptides. Accordingly, MDCs were obtained and enriched from a starting muscle cell suspension by plating the suspension into at least two successive cultures so as to eliminate fibroblasts and non-muscle cells and to enrich for an end population of mononucleated, early muscle-derived cells or myoblasts.

For particular experiments using mice, mouse hindlimb skeletal muscles were removed and the bones were dissected away. The muscle was then minced into a coarse slurry using scalpels. The muscle tissue was enzymatically dissociated at 37° C. in 0.2% collagenase-Type XI (Sigma-Aldrich) for 1 hour, and then centrifuged at 3500 rpm for 5 minutes. The cells were collected, incubated in dispase (GIBCO BRL) prepared as 2.4 U/ml HBSS (GIBCO BRL) for 45 minutes, and then incubated for 30 minutes in 0.1% trypsin-EDTA (GIBCO BRL) diluted in HBSS. After the enzymatic dissociation, the muscle cells were again centrifuged at 3500 rpm and resuspended in proliferation medium (PM) containing DME, supplemented to contain 10% horse serum, 10% FBS, 0.5% chick embryo extract and 1% penicillin-streptomycin (all purchased from GIBCO BRL).

In these experiments, MDCs were isolated following a serial culture transfer procedure involving successive passages using containers such as tissue culture flasks (or plates), e.g., T25, T50, T150, (See also, U.S. Pat. No. 6,866,842 and U.S. Pat. No. 7,115,417) to culture the cells. The containers can be collagen-coated (collagen type 1, Sigma Aldrich). Following initial resuspension in PM, the starting muscle cell suspension in this experiment was plated in collagen-coated flasks, e.g., for about 2 hours. After allowing fibroblasts to adhere, e.g., about 1-2 hours, the nonfibroblast cells were transferred to other flasks. After about a day, e.g., 24 hours, in which the cells were housed in an incubator at 37.degree. C., 100% humidity, 95% air/5%

CO.sub.2, the viable cells in the flasks were collected, centrifuged at 3500 rpm for about 5 minutes, and plated in new flasks. In general, at this time, about $1 \times 10^4$-$5 \times 10^4$ viable cells were transferred to new culture plates. This procedure of serial transfer and plating of the viable cells into new culture plates/flasks was repeated, e.g., at about 24 hour intervals, until in later platings (also called "preplates"), fibroblasts were depleted and the cultures were enriched in desmin positive, early muscle-derived myoblastic cells. At the end of the serial plating procedure, i.e., at the time of the last plating, an enriched end population of MDCs comprised viable, growing, desmin-positive (greater than about 50%), mononucleated muscle-derived cells that were used for injections and were able to generate muscle fibers.

The serial plating and culture technique was carried out over a period of days until only MDCs that were depleted of fibroblasts and non-muscle cells, and enriched for mononucleated myoblastic cells remained viable and growing in the culture plates. The serial plating and culture process to attain viable MDCs in the cultures involved from about 3 to 7 days, or about 3-6 days, after initial plating of the muscle cell sample. The successive transfer and plating of the non-fibroblast cells to new plates/flasks allowed for an enrichment of non-fibroblastic, mononucleated, desmin-positive early MDCs that generated myofibers in appropriate environments after injection into animals.

Flow Cytometry:

To determine surface marker expression, MDCs were incubated with both direct and biotin-conjugated rat anti-mouse monoclonal antibodies (e.g., antibodies specific for c-kit, CD34, CD56, Sca-1, and CD45; all antibodies from Pharmingen) for 30 minutes, and streptavidin-allophycocyanin conjugate was added to the cells labeled with biotinylated antibodies for 20 minutes. The labeled cells were analyzed on a FACSCalibur (Becton Dickinson, San Jose, Calif.) flow cytometer using Cell Quest software.

Histology:

Muscle and tissue sections were fixed in 1% glutaraldehyde, incubated overnight with X-gal substrate at 37° C., and then counterstained with eosin. β-Galactosidase/GFAP/Hoechst co-localization to reveal donor-derived cells was performed with primary antibodies against mouse anti-β-galactosidase (1:100, Chemicon, Temecula, Calif.).

Statistical Analysis:

Measurements of nerve area, as well as the diameter of myofibers in MDC- and sham-injected tissues, were performed by computerized image analysis of muscle sections stained by histochemistry and immunohistochemistry. A paired t test was used to compare the differences between MDC- and sham-injected tissues. A level of $P<0.05$ was considered significant for the differences between mean values.

Example 2

This Example describes neurorecovery and improved erectile function using MDCs in a rat model of post-radical prostatectomy erectile dysfunction. Despite advances in surgical techniques, erectile dysfunction (ED) is a common outcome in men undergoing radical prostatectomy. In response to environmental cues and, in accordance with the present invention, MDCs were found to promote and/or enhance axonal regeneration in the central and peripheral nervous systems. In view of the ability of MDCs to facilitate the regeneration of peripheral nerve, experiments were performed to assess MDCs as a therapy for post radical prostatectomy erectile dysfunction.

A skeletal muscle biopsy was taken from the hind limb of a normal adult mouse and subjected to the preplate technique to obtain MDCs as described. Allogeneic mouse MDCs isolated from the plating/culturing technique (i.e., at approximately 5-6 days of serial culture, were transduced with retrovirus engineered to express the β-galactosidase reporter gene. Cavernous nerve transection in rats was used as a model of post radical prostatectomy erectile dysfunction. The three experimental groups included: (1) a control group (C, n=5); (2) a bilateral cavernous nerve transected group with sham injection (T, n=6); and (3) a bilateral cavernous nerve transected group which received MDC injections ($3 \times 10^5$ cells/each side) at the site of transection (M, n=6). Two weeks after surgery, a PE 20 tube connected to a pressure transducer was inserted into the cavernosum and intracavernous pressures (ICP) were measured during electrical stimulation (20 Hz, 0.5 ms, 10V) of the pelvic nerve. The animals were then sacrificed and the tissues surrounding the site of cavernous nerve transection were removed for LacZ staining.

The maximal ICPs for the C, T and M groups were 115±11.2 cmH$_2$O, 25.4±6.6 cmH$_2$O, and 52.5±9.5 cmH$_2$O, respectively. The ICP of the MDC treated group (group M) was significantly greater than the sham-injected group ($p<0.05$). Staining for LacZ revealed many LacZ (+) cells around the MDC-injected area. The results demonstrate immunohistological and functional evidence for the capacity of MDCs to repair injured peripheral nerves and improve erectile function. In accordance with the present invention, erectile dysfunction is a candidate condition for treatment using MDCs at the time of radical prostatectomy.

Example 3

MDCs according to this invention are used in an animal model for burn-related peripheral nerve damage. An area of 2.5 cm$^2$ full-thickness skin is excised from the backs of nude mice to mimic the effects of severe burns. In the experimental group, MDCs according to the invention are applied to the full area of injury prior to the transplantation of a tissue-engineered skin substitute. In the control group, no MDCs are applied prior to transplantation. The skin substitute comprises a collagen sponge matrix seeded with human keratinocytes and fibroblasts. Mice are sacrificed at 40, 70, and 120 days post transplantation and biopsies of the reconstructed skin are subjected to immunohistochemical and histological analyses for evidence of nerve regeneration and innervation. Axons are detected by antibody staining for protein gene product 9.5 (PGP 9.5), a specific phenotypic marker for neuronal cells. The presence and abundance of Schwann cells in and around transplanted tissue is examined via antibody staining for protein S100, a calcium-binding protein expressed in glial cells.

Example 4

This Example describes a clinical study and protocol, and related experimentation, to investigate a treatment to prevent, reduce, or ameliorate the problems of stress urinary incontinence and erectile dysfunction at the time of radical prostatectomy surgery by injecting autologous MDCs.

Men at least 18 years of age with prostate cancer and who are about to undergo radical prostectomy surgery, and having tested negative for Hepatitis B, Hepatitis C, HIV and bovine protein allergies are eligible for study participation. Eligible patients consenting to study participation visit the urology clinic for an initial outpatient procedure in which muscle cells are harvested using a needle biopsy technique. Specimens are processed by a successive cell plating/culturing technique which results in an enriched end population of non-fibroblast, viable, proliferating, mononucleated, muscle-derived cells (myoblast cells) that can give rise to myotubes. Cell processing follows good tissue practices to prevent contamination and to preserve tissue function and integrity, and includes defined procedures for tissue and cell handling, processing, and identification. The enriched end population of MDCs is expanded in culture to obtain increased numbers of cells for subsequent use.

Several weeks later, the isolated and expanded MDCs are frozen and shipped to the investigating physician. The expanded MDCs are supplied to the physician frozen in a cryogenic medium containing Human Serum Albumin (HSA). The MDCs are then thawed and diluted with physiological saline for injection into the patient by the physician or clinician. Materials contacting patient periurethral tissue include the patient's own MDCs, the cryogenic medium in which it is suspended and shipped, and the physiological saline used to dilute the mixture for injection.

The resulting suspension is injected into the patient's urethral anastomosis at the time of his radical prostatectomy surgery under direct vision. Patients are assessed for the occurrence of adverse events and urinary incontinence and sexual function at 1, 3, 6, and 12 months following treatment. If there is no improvement at the 6-month follow-up, patients may choose to have repeat treatment with the muscle cell injection, through a brief outpatient cystoscopic injection procedure, without repeating the muscle biopsy.

The initial treatment effect is expected to arise from the added physical bulk resulting from the injected MDC suspension. However, the cells can remain viable and persist where injected for a longer-term effect. Ultimately, and without wishing to be bound by theory, the tissue environment "instructs" the injected MDCs to remodel into tissue resembling natural urethral sphincter, which, in turn, improves incontinence over time. Moreover, injection of MDCs at site of radical prostatectomy anastomosis can serve to protect the penile nerves during recovery and promote or enhance return of erectile function.

This Example encompasses a small scale, single center study of up to 20 patients, intended to identify the safety and potential effectiveness of the proposed treatment. Patients serve as their own controls, with quantitative and qualitative measures of incontinence and erectile function assessed before treatment and at various times after treatment. Patients are followed for one year after treatment. For injection, autologous MDCs are suspended in physiological saline.

The following protocol is employed at the time of radical prostatectomy surgery:

1. Using standard techniques, the patient is prepared for radical prostatectomy. The MDC injection is performed at the conclusion of the surgery, after the prostate has been removed, and the bladder neck and urethra have been reanastomosed.
2. The frozen MDC suspension is thawed by diluting with an equal volume of physiological saline and is drawn into a syringe.
3. Prefilled syringe is attached to syringe needle according to manufacturer's instructions for use.
4. Under direct vision, insert the needle tip into the urethra and periurethral tissue and slowly inject the prepared MDC suspension. This is done at three locations around the anastomosis.
5. Record position(s) and volume of cell suspension injected.

At time of cystoscopic injection at 6 months, if there is no improvement and patient requests the repeat injection, the following protocol is followed:

1. Using standard techniques, the patient is prepared for cystoscopy with the administration of appropriate anesthesia for insertion of cystoscope.
2. Prepare cystoscope with lens and transurethral needle, being careful to see that the needle tip is contained within the distal cystoscope sheath.
3. Carefully advance cystoscope to desired location.
4. Thaw the MDC suspension by diluting with an equal volume of physiological saline and draw into syringe.
5. Attach prefilled syringe to cystoscope according to manufacturer's instructions for use.
6. Under direct vision, insert the needle tip into the urethral sphincter mechanism and slowly inject the prepared MDC suspension into the submucosal urethral wall.
7. Continue injection until urethral closure is observed, using multiple periurethral locations if necessary.
8. Record position(s) and volume of cell suspension injected.

Training and experience needed for use of MDC injection includes familiarity with radical prostatectomy, cystoscopy and injection of periurethral bulking agents.

Clinicians and physicians skilled in the art appreciate that stress urinary incontinence and erectile dysfunction are the two most common and bothersome complications of a radical prostate cancer operation. Stress urinary incontinence due to intrinsic sphincteric deficiency (ISD) results from an intrinsic malfunction of the distal urethral sphincter. In men, ISD usually develops following radical prostatectomy. The prevalence of postprostatectomy incontinence continues to rise, paralleling the increase in surgical procedures performed annually. In one series of 60 patients, 67% of postprostatectomy incontinence was due to ISD alone, using the LPP technique as the basis for this assessment (Carlson, K. V. and Nitti, V. W., Prevention and management of incontinence following radical prostatectomy. *Urol Clin North Am,* 28: 595, 2001). In another study, a prospective urodynamic evaluation was performed in 20 patients who had undergone radical prostatectomy; a postoperative intrinsic urethral sphincter pressure component was found in 17 of the 20 patients. (Pfister, C. et al., Assessment of the intrinsic urethral sphincter component function in postprostatectomy urinary incontinence. *Neurourol Urodyn,* 21: 194, 2002).

Erectile dysfunction (ED) is defined as the consistent inability to achieve or maintain an erection adequate for sexual satisfaction. ED is estimated to affect up to about 30 million men in the United States alone (World Health Organization International Consultation on Impotence. (WHO, 1$^{st}$ International Consultation in Impotence, Plymbridge Distributors Ltd, Plymouth, UK, 1998). Quality of life data have documented the importance of erectile dysfunction to other chronic health conditions such as depression. As such, ED is devastating not only to the affected male but also to their sexual partner. Despite advances in surgical techniques, ED still commonly occurs after men undergo radical prostatectomy. Recovery can be protracted in those whose erections do return, with slow improvements in the initiation and sustaining of an erection observed up to 36 months post operatively. The trauma associated with removing the prostate overlying the neurovascular bundles can produce neuropraxia. Furthermore, local inflammation and immune response can also cause ED. Conventional treatment, such as Viagra, is not always effective or safe for men with history of cardiovascular disease.

Nonclinical testing of MDC injection into the lower urinary tract has been conducted in a number of animal studies. In summary, such studies include: 1) a preliminary evaluation of MDC persistence and differentiation after injection in the bladder wall of a mouse model; 2) an assessment of injected MDC persistence as compared to injected bovine collagen in an autologous rat model; 3) assessment of periurethral injected allogeneic MDCs in a rat incontinence model; 4) MDC result in postprostatectomy incontinence model; and 5) effect of MDC injection of erectile dysfunction in prostectomy model. Such studies provide feasibility models for human treatment using MDCs and injection following prostate surgery.

Model of Stress Incontinence Postprostatectomy:

To produce intrinsic sphincter deficiency like that of post radical prostatectomy SUI in human patients, surrounding tissues lateral to the mid-urethra were cauterized in adult female Sprague-Dawley rats (n=16). One week after cauterization, $1.5 \times 10^6$ MDC, transfected with Lac Z, were injected peri-urethrally into the mid-urethra. The 16 rats were divided into 3 groups, evaluated at 2, 4, or 6 weeks after MDC injection. As a control, 9 rats underwent cauterization followed by injection with Hanks' Balanced Salt Solution (HBSS) one week later. Sphincteric function was studied using the vertical tilt table/intravesical pressure clamp technique to measure leak point pressures (LPPs). The location of the MDC was assessed using fast myosin heavy chain and Lac Z staining.

Electrocautery of the urethra had no effect on bladder function. The mean LPPs of the rats 2, 4, and 6 weeks after MDC injection were $38.2 \pm 2.2$ cm $H_2O$, $43.1 \pm 2.6$ cm $H_2O$, and $51.5 \pm 0.9$ cm $H_2O$, respectively. The mean LPPs of the rats 2, 4, and 6 weeks after HBSS injection were $17.2 \pm 1.4$ cm $H_2O$, $26.9 \pm 1.9$ cm $H_2O$ and $25.5 \pm 1.3$ cm $H_2O$, respectively. When compared to time-matched control groups, the increased LPPs in each MDC injected group were significantly higher ($p<0.001$). Histological analysis showed that the MDC contributed to striated muscle and nerve regeneration. Thus, the injection of periurethral MDC repaired the damaged urethral sphincter in rats with ISD.

Model of Erectile Dysfunction Post Prostatectomy:

The nerve innervating the cavernosum is crucial in initiating and sustaining an erection in males. Injury to this nerve is the main source of erectile dysfunction after a radical prostatectomy. The purpose of this experiment was to determine whether MDCs promote and/or enhance peripheral axonal regeneration, thus resulting in a faster recovery of erection dysfunction in a rat model of radical prostatectomy.

In this experiment and similar to that described in Example 2, MDCs were obtained from the skeletal muscle via successive culturing, as described herein, to enrich for early muscle-derived cells including myoblasts. Cavernous nerve transection was used as a model of post radical prostatectomy erectile dysfunction. The three experimental groups included a control group (C, n=6); a bilateral cavernous nerve transected group (T, n=6); a bilateral cavernous nerve transected and vehicle injection group (V, n=6); and a bilateral cavernous nerve transected group with MDC injections ($3 \times 10^5$ cells/each side) at the site of injury (M, n=6). Two weeks after surgery, the symphysis pubis was cut and the pelvic bone was retracted laterally to expose the distal cavernous nerve. A stimulating electrode was placed on the pelvic nerve and a recording electrode was placed distal to the injury site. Compound action potentials (CAP) were measured after each stimulus (X Hz, 0.25 ms, 10V). A PE 20 tube connected to a pressure transducer was inserted into the cavernosum and intracavernous pressures (ICP) were measured during electrical stimulation (20 Hz, 0.5 ms, 10V) of the pelvic nerve.

The results from this experiment showed that the amplitude of the CAP of the cavernous nerve was greater in the M group compared with the T and V groups. However, CAPs of the M group were not as large as those of the control group. The mean maximal ICP for the M group ($52.5 \pm 9.5$ cm$H_2O$) was also significantly greater than that of the T group ($25.4 \pm 6.6$ cm$H_2O$), ($p<0.05$). The ICP of the C group was $115 \pm 11.2$ cm$H_2O$. This analysis demonstrated that CAP may serve as a good indicator of nerve recovery as observed from its correlation with ICP after electrical field stimulation. Application of MDC facilitated the recovery of the CAP and improved erectile function in cavernous injured rats compared with the injury in only sham injected groups. Accordingly, in a model of ED involving damage to the penile nerve, injection of MDCs around the site of nerve damage improved erectile function, thus supporting the use of MDCs as facilitators for the recovery of erectile dysfunction after a radical prostatectomy.

Risk Analysis and Assessment:

The risks associated with radical prostatectomy in human males are completely separate from the injection of MDCs. Risks associated with participation in the clinical study involving MDC injection to treat ED include related to the following:

Cystoscopy:

The risks of cystoscopy are expected to be infrequent (occurring in 1-10% of people), and include the possibility of discomfort, bleeding, and infection. Side effects that are rare (expected to occur in less than 1% of people) include inability to urinate after the procedure and puncture of the bladder.

Muscle Biopsy:

The risks of muscle biopsy are expected to be infrequent, (occurring in 1-10% of people) and include the possibility of wound infection, hematoma, and pain.

Venipuncture:

The risks from venipuncture include bleeding, discomfort, light-headedness, pain, bruising, and rarely, an infection at the site where blood is drawn.

Cellular Injection:

The potential risk from the cellular injection includes an immune response, although this risk is expected to be minimal because autologous cells are used and patients are screened for potential reaction to the trace of bovine proteins that may be present.

Urinary Catheterization:

The risks of urinary catheterization are expected to be infrequent (occurring in 1-10% of people), and include the possibility of transient inability to void, discomfort during catheter insertion, urinary tract infections, bleeding and discomfort or pain.

Urodynamic Study:

The risks of urodynamic study are similar to urinary catheterization and include possibility of transient inability to void, discomfort during insertion of the catheter, urinary tract infection, and bleeding.

Bovine Skin Prick Test:

The potential risk from the skin prick allergy test to determine if a patient is allergic to bovine (cow) protein can include a small amount of bleeding, pain, skin rash, or possibly anaphylactic shock.

Additional risks are expected to be comparable to those associated with standard treatment using collagen injections and include the possibility of continued incontinence, increased incontinence, urinary retention, infection, bladder outlet obstruction, fever, tumor formation, displacement of injected material and an allergic reaction to the injected reagents. The risks of cellular injection are expected to be minimal due to the use of autologous cells and based on satisfactory results in animal model studies.

Objectives of the Clinical Investigation:
Claims and Intended Performance to be Verified The objective of the study is to identify the safety and potential effectiveness of the proposed treatment. The intended performance of the MDC treatment includes reasonable safety in terms of the incidence of residual urine volume, urinary tract infection, other adverse events, and effectiveness in preventing urinary incontinence and sexual dysfunction in terms of improved patient quality of life (QOL), leak point pressure (LPP), number of incontinence episodes per 24 hour period.

Risks and Foreseeable Adverse Effects to be Assessed

The risks of bleeding and puncture are assessed by cystoscopy after injection. The risks of continued incontinence, urinary tract infection, urinary retention, displacement of injected cells, and allergic reaction to the injected reagents is assessed through patient report, a recorded patient voiding diary and clinical follow-up at 1, 3, 6, and 12 months after treatment.

Specific Hypotheses to be Evaluated

The hypotheses to be evaluated are that the MDC treatment is reasonably safe in terms of the incidence of bleeding, puncture, urinary tract infection, and post void residual, and evidence of effectiveness is observed in improved quality of life (QOL), reduced number of incontinence episodes per 24 hour period and increased LPP and improvement in erectile function.

Design of the Investigation:
Description of Type of Investigation to be Performed with Rationale for Choice This study is designed as a small scale, single center, prospective study in which up to 20 patients serve as their own controls. This design is appropriate for preliminary identification of the safety and potential effectiveness of the proposed treatment.

Control Population

Patients serve as their own controls in this study, with quantitative and qualitative measures of incontinence assessed before treatment compared to the same measures assessed at various times after treatment.

Measures Taken to Avoid Bias

Reliance on objective measures such as bladder diary including 24 hour pad collection and frequency of incontinent episodes serves to minimize the potential for bias with use of patients as their own controls.

Primary and Secondary Endpoints (Outcomes)

Primary endpoints include: incidence of adverse events; valsalva LPP as observed through urodynamic study; frequency of incontinent episodes recorded in bladder diary; and UCLA Prostate Cancer continence and sexual function scores. Secondary endpoints include: patient quality of life/patient satisfaction survey (at exit); and residual urine volume.

Variables to be Measured with Rationale for Their Selection

Variables to be assessed in study participants include medical history, vital signs, bladder diary, sexual function, CBC, blood chemistry, urinalysis, pregnancy status, extent of urethral hypermobility (if present), residual urine volume and urethral appearance via cystoscope, leak point pressure via urodynamics.

Methods and Timing for Assessing, Recording and Analyzing Variables

Standardized data forms are used for recording data. Medical history, physical examination, vital signs, CBC, blood chemistry, urinalysis, and pregnancy status are determined by standard methods. Continence and sexual function are assessed through the bladder diary and by completion of the UCLA Prostate Cancer Index. The visual appearance of the urethra and bladder is evaluated by cystoscopy. The leak point pressure (LPP) is evaluated through urodynamics. Post void residual urine volume is assessed by standard ultrasound technique. The timing for assessment of variables is presented in the following Schedule of Events table:

| EVENT | SCREEN | BIOPSY | RRP/INJECTION | M-1 | M-3 | M-6 | M-12 |
|---|---|---|---|---|---|---|---|
| Medical history | x | | | | | | |
| Vital signs | x | x1/x2 | x1/x2 | x | x | x | x |
| Medications list | x | x | | x | x | x | x |
| Physical examination | x | | | | | | x |
| Allergy Skin Test | x | | | | | | |
| Urodynamic study | | | | | | x | |
| Cystoscopy | | | | | | x | |
| Residual urine volume (by US) | x | | | x | x | x | x |
| Bladder diary distributed (including 24 hour pad collection) | x | | | x | x | x | x |
| UCLA Prostate Cancer Index | x | | | x | x | x | x |
| Global improvement questionnaire | x | | | x | x | x | x |
| Occurrence of adverse events | | x2 | x | x | x | x | x |
| Bladder diary reviewed | | x | | x | x | x | x |
| Lab: | | | | | | | |
| CBC / Blood chemistry | x | | | | | | x |
| Bloodborne virus | x | | | | | | |

-continued

Schedule of Events

| EVENT | SCREEN | BIOPSY | RRP/INJECTION | M-1 | M-3 | M-6 | M-12 |
|---|---|---|---|---|---|---|---|
| Urine Culture | x | | | | | | |
| Urinalysis (including dipstick*) | x | | x | x | x | x | x |

M-1: month 1 post injection
x1: before biopsy / injection
*a positive dipstick test will require urine culture
x2: after biopsy / injection In addition to the scheduled events presented in the table, patients are contacted by telephone within 24 to 48 hours of injection to assess the occurrence of any untoward effects. Follow-up for patients who receive a second injection at 6 months reverts to the schedule for the first injection (i.e., 24-48 hrs, and 1, 3, 6, and 12 months following), for a total time in the study of either 15 or 18 months.

Inclusion and Exclusion Criteria

Men eligible for study participation shall meet the following inclusion criteria: (i) have provided written informed consent; (ii) are at least 18 years of age; (iii) have localized prostate cancer and are scheduled for radical prostatectomy surgery; (iv) have viable mucosal lining along urinary tract and in bladder; (v) have tested negative for hepatitis B, hepatitis C, and HIV; (vi) have tested negative for sensitivity to possible trace amounts of bovine protein; (vii) have a negative urine culture, or positive culture with expectation of clearing by time of treatment; (viii) have a life expectancy of at least 1 year; (ix) agree to be available for the follow-up evaluations as required by the protocol; and (x) have PTT INR within normal range. Men meeting any of the following exclusion criteria shall be excluded from enrollment: (i) have known vesicoureteral reflux, overactive bladder, detrusor instability, or high pressure instability; (ii) are on current medication for urge incontinence; (iii) have urinary incontinence of neurogenic etiology; (iv) have an indwelling catheter; (v) have neuromuscular disorders (e.g., muscular dystrophy, multiple sclerosis); (vi) have diabetes; (vii) have fibrosis of the tissue at the likely injection sites; (viii) have any condition which could lead to significant postoperative complications, including current infection, or elevated residual urine from bladder outlet obstruction (i.e., repeated PVR>150 mL); (ix) are morbidly obese (defined as 100 pounds over their ideal body weight) and would not be expected to benefit from treatment; (x) have current or acute conditions involving cystitis or urethritis; (xi) have a compromised immune system due to disease state or chronic steroids or immunosuppressives; or (xii) have any condition that would preclude treatment due to contraindications and/or warnings in the experimental or control product labeling.

After consenting to study participation and meeting all entry criteria, patients are enrolled in the study at the time of collection of the muscle biopsy. Patients consenting to participation in the study and meeting study entry criteria are instructed in methods for completing a three day study diary. A bladder and sexual function questionnaire and a global improvement questionnaire are completed. Patients also have blood and urine samples collected for laboratory analysis including screening for bloodborne viruses. Patients undergo ultrasound for determination of residual urine volume. In addition, patients undergo an allergy skin test to determine if they are sensitive to possible trace amounts of bovine proteins.

Approximately two weeks later, patients visit the urology clinic for an initial outpatient procedure in which muscle cells are harvested using a needle biopsy technique. Approximately four weeks after biopsy, patients return to the hospital for their radical prostatectomy surgery in which the patient's own processed cells are injected periurethrally using a small needle. Patients also provide their study diaries for assessment, complete QOL and global improvement questionnaires, have a urine sample collected for laboratory analysis, and have their residual urine volume determined by ultrasound.

At about 24 to 48 hours after injection, patients are contacted by phone call to determine if any untoward effects have occurred. Patients return for follow-up at 1, 3, 6, and 12 months. At each follow-up, patients provide their bladder diaries including 24 hour pad collection, complete a QOL questionnaire, have blood and urine samples collected for analysis, and undergo ultrasound for determination of residual urine volume. At the 6-month time point, patients also undergo cystoscopy for evaluation of the appearance of urethral tissue, and a urodynamics study to evaluate leak point pressure. If there is no improvement at the 6-month follow-up, patients may choose to have repeat treatment with the muscle cell injection, without repeating the muscle biopsy. Follow-up in this case reverts to the schedule for the first injection (i.e., 24-48 hrs, and 1, 3, 6, and 12 months following). A biopsy needle is used for muscle tissue harvesting. Physiological saline is used for dilution and thawing of the frozen MDCs, which are frozen in a cryogenic medium containing HSA. The MDCs may contain traces of bovine serum.

Patients remain in the study until having completed a 12-month follow-up after injection of their MDCs. If at any time patients state they no longer wish to participate, they may withdraw without prejudice or loss of care. At the discretion of the Principal Investigator, patients may be withdrawn from the study if it is deemed in the best interest of their medical care. Patients who choose to withdraw from the study are asked to complete the exit visit procedures, but are not obligated to do so.

Up to 20 patients are planned for the study. It is anticipated that enrollment could be completed in one year. Every enrolled patient receives one initial injection with an additional injection allowed at the 6-month follow-up if the patient is without improvement or has returned to baseline. Patients are followed for one year from last injection. Patient tissue samples are retained by the sponsor for 18 months following injection of MDCs, and are subsequently destroyed.

Example 5

This Example describes MDC-induced neurorecovery in a rat model of bladder peripheral neuropathy. Trauma to the pelvic nerves during radical pelvic surgeries such as prostatectomy is common and can lead to serious voiding dysfunctions. These dysfunctions are refractory to most current treatments. The application of MDCs in or around the site of pelvic nerve damage represents a new method of treating neurogenic voiding disorders.

Methods:

MDCs were isolated from the gastrocnemius muscle of normal adult rats and purified via the plating and culturing technique as described earlier. Unilateral pelvic nerve transection was used to study peripheral nerve regeneration in adult female rats. Three experimental groups included: (C) control group (n=5); (S) unilateral pelvic nerve transected group with sham injection (n=5); (M) unilateral pelvic nerve transected group with MDC injection ($3 \times 10^5$ cells/site) (n=5). Two weeks after injection, intravesical pressures were measured during electrical stimulation of the proximal transected preganglionic pelvic nerve. Immediately prior to stimulation, the contralateral (uninjured) major pelvic ganglion (MPG) was excised in order to ensure that any observed bladder activity was due exclusively to inputs from the unilateral (injured) side. Following experiments, rats were sacrificed and the unilateral MPG was removed and assayed for enkephalin immunoreactivity (ENK-IR) to assess the survival of bladder-projecting neurons.

Results:

Two weeks after surgery, the maximal intravesical pressures for C, S, and M groups were, respectively, $31.7 \pm 10.3$ cmH$_2$O, $9.6 \pm 4.5$ cmH$_2$O, $15.2 \pm 7.7$ cmH$_2$O. Compared with normal control animals (C), the pressure responses of the sham-injected rats (S) were reduced significantly ($p<0.01$). Compared with the S group, the pressure responses of the M group were significantly greater ($p<0.01$) but did not reach normal levels. After transection of the preganglionic pelvic nerve, the intensity of pericellular enkephalin-immunoreactive (ENK-IR) varicosities was more markedly decreased in the S group than in the M group. In the S group, the area positively stained with enkephalin in the MPG was significantly ($p<0.001$) reduced compared to the C group ($47.6 \pm 2.3$ vs. $87.0 \pm 3.5\%$ of the total MPG area). However, the area positively stained with enkephalin in the MPG was not significantly different between C and M groups ($92.1 \pm 3.3\%$ vs. $88.7 \pm 2.0\%$). These results demonstrate that MDCs can promote neuronal survival and regeneration in a peripheral nerve injury model.

All patent applications, published applications, patents, texts, treatises, and literature references as cited in this specification are hereby incorporated herein by reference in their entireties to more fully describe the state of the art to which the present invention pertains.

As various changes can be made in the above methods and compositions without departing from the scope and spirit of the invention as described, it is intended that all subject matter contained in the above description or defined in the appended claims be interpreted as illustrative, and not in a limiting sense.

What is claimed is:

1. A method of protecting penile nerve during recovery after a radical prostatectomy anastomosis in a human subject in need thereof, comprising:
    injecting a cell suspension of isolated autologous adult human muscle-derived cells (MDCs) into said subject at the urethra or periurethral tissue at the time of the radical prostatectomy anastomosis, wherein said isolated MDCs are injected in an amount effective to protect the penile nerve, wherein the protection of the nerve during recovery treats erectile dysfunction and/or urinary incontinence; wherein the MDCs are enriched from a muscle cell suspension by plating the suspension into at least two successive cultures so as to eliminate fibroblasts and non-muscle cells and to enrich for an end population of mononucleated MDCs, wherein the enriched end population of mononucleated MDCs comprises myoblasts; wherein the MDCs are not genetically engineered to express heterologous genes and wherein the MDCs are introduced in an amount of about 105 to 106 cells per cm3 of tissue or organ in a physiologically acceptable medium.

2. The method according to claim 1, wherein the MDCs are obtained from skeletal muscle tissue.

3. The method according to claim 1, wherein a cloned population of the MDCs is introduced into the human subject.

* * * * *